United States Patent [19]

Sauerberg et al.

[11] Patent Number: 5,260,311
[45] Date of Patent: * Nov. 9, 1993

[54] PIPERIDINE COMPOUNDS AND THEIR USE

[75] Inventors: Per Sauerberg, Valby; Preben H. Olesen, Kobenhavn, both of Denmark

[73] Assignee: Novo Nordisk A/S, Bagsvaerd, Denmark

[*] Notice: The portion of the term of this patent subsequent to Aug. 20, 2008 has been disclaimed.

[21] Appl. No.: 746,378

[22] Filed: Aug. 16, 1991

Related U.S. Application Data

[63] Continuation of Ser. No. 482,272, Feb. 20, 1990, Pat. No. 5,041,455, which is a continuation-in-part of Ser. No. 401,370, Aug. 31, 1989, Pat. No. 5,043,345.

[30] Foreign Application Priority Data

Feb. 22, 1989 [DK] Denmark .............................. 0825/89
May 12, 1989 [DK] Denmark .............................. 2315/89

[51] Int. Cl.⁵ .................. C07D 417/04; A61K 31/44
[52] U.S. Cl. ..................................... 514/342; 546/277
[58] Field of Search ...................... 546/277; 514/342

[56] References Cited

U.S. PATENT DOCUMENTS

| | | | |
|---|---|---|---|
| 4,837,241 | 6/1989 | Jensen et al. | 514/340 |
| 4,866,077 | 9/1989 | Bogeso et al. | 514/326 |
| 4,933,353 | 6/1990 | Jensen et al. | 514/340 |
| 4,952,587 | 8/1990 | Baker et al. | 514/305 |
| 5,041,455 | 8/1991 | Sauerberg et al. | 514/342 |
| 5,043,345 | 8/1991 | Sauerberg et al. | 514/342 |

FOREIGN PATENT DOCUMENTS 0296721 12/1988 European Pat. Off. .
0307142  3/1989 European Pat. Off. .

OTHER PUBLICATIONS

Appel Current Neurology, pp. 289, 315, 1987.

*Primary Examiner*—Jane T. Fan
*Attorney, Agent, or Firm*—Steve T. Zelson; Elias J. Lambiris

[57] ABSTRACT

The present invention relates to therapeutically active piperidine compounds, a method of preparing the same and to pharmaceutical compositions comprising the compounds. The novel compounds are useful as stimulants of the cognitive function of the forebrain and hippocampus of mammals and especially in the treatment of Alzheimer's disease, severe painful conditions and glaucoma.

15 Claims, No Drawings

PIPERIDINE COMPOUNDS AND THEIR USE

CROSS-REFERENCE TO RELATED U.S. APPLICATION

This application is a continuation application of Ser. No. 07/482,272 filed Feb. 20, 1990, now U.S. Pat. No. 5,041,455 which issued on Aug. 20, 1991, which is a Continuation-in-Part of U.S. patent application Ser. No. 07/401,370 filed on Aug. 31, 1989, now U.S. Pat. No. 5,043,345 which issued on Aug. 27, 1991.

Due to the in general improved health situation in the western world, elderly-related diseases are much more common now than in the past and are likely to be even more common in the future.

One of the elderly-related symptoms is a reduction of the cognitive functions This symptom is especially pronounced in the pathophysiological disease known as Alzheimer's disease. This disease is combined with, and also most likely caused by, a up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic muscarinic receptors in the forebrain and hippocampus still exist. Therefore, muscarinic cholinergic agonists are useful in the treatment of Alzheimer's disease and in improving the cognitive functions of elderly people.

It is well known that arecoline (methyl 1-methyl-1,2,5,6-tetrahydropyridine-3-carboxylate) is such a cholinergic agonist (See Formula A)

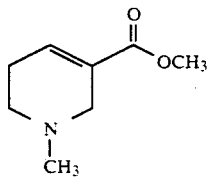

(A)

Arecoline, however, has a very short biological half life and a small separation between central and peripheral muscarinic effects. Furthermore, arecoline is a rather toxic compound. It is also known that 3-acetoxy-quinuclidine is a muscarinic agonist (See Formula B)

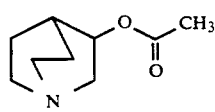

(B)

However, the disadvantages of this compound are the same as indicated for arecoline.

It is, therefore, an object of the present invention to provide new muscarinic cholinergic compounds having different structures and different levels of activity.

The novel compounds of the invention are of formula I:

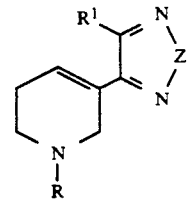

(I)

wherein Z is oxygen or sulphur, R is H, $C_{1-3}$-alkyl, $C_{3-4}$-cycloalkyl, $C_{2-4}$-alkenyl or $C_{2-4}$-alkynyl and $R^1$ is $C_{1-15}$-alkyl, $C_{2-15}$-alkenyl, $C_{2-15}$-alkynyl, $C_{3-7}$-cycloalkyl, $C_{4-8}$-cycloalkylalkyl, phenoxy, benzyloxy, morpholino, $C_{1-6}$-alkyl substituted piperidino, halogen, amino, $C_{1-6}$-acylamino, $C_{1-15}$-alkylamino, $C_{1-15}$-dialkylamino, $C_{1-15}$-alkoxyamino, S-$R^2$ or O—$R^2$ wherein R2 is straight or branched $C_{1-15}$-alkyl, straight or branched $C_{2-15}$-alkenyl, straight or branched $C_{2-15}$-alkynyl, $R^3$—O—$R^4$, $R^3$—NH—$R^4$, $R^3$—S—$R^4$, $R^3$—O—$R^4$—O—$R^5$ wherein $R^3$, $R^4$ and $R^5$ independently are $C_{1-15}$-alkyl, $C_{2-15}$-alkenyl, $C_{2-15}$-alkynyl or a salt thereof with a pharmaceutically-acceptable acid.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic and organic acid addition salts.

This invention also includes a method for producing compounds of formula I with alkylation and reduction reactions of the appropriate pyridine compounds. In addition, the invention herein further comprises pharmaceutically compositions incorporating the compounds of formula I along with methods for treating Alzheimer's disease with these compounds.

The compounds of this invention are also useful analgesic agents and therefore useful in the treatment of severe painful conditions.

Furthermore, the compounds of this invention are useful in the treatment of glaucoma.

The invention comprises a method of preparing 3-(1,2,5-oxadiazol-3-yl) or 3-(1,2,5-thiadiazol-3-yl)-1,2,5,6-tetrahydropyridine compounds having the general formula I:

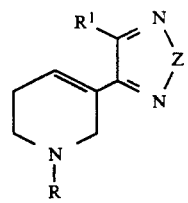

(I)

by alkylating a compound having the formula II

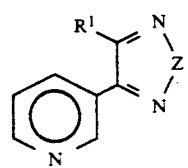

(II)

with an alkyl halide and reducing the compound thus formed with hydride ions to form a compound having the formula I

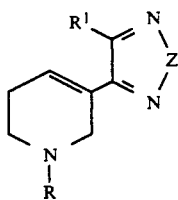
(I)

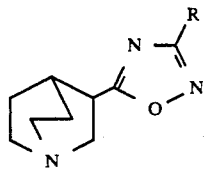
VII

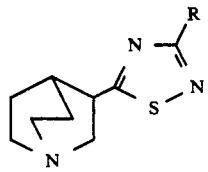
VIII

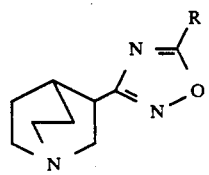
IX

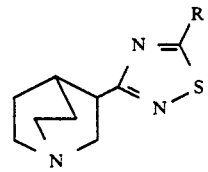
X wherein Z is oxygen or sulphur, R is H, $C_{1-3}$-alkyl, $C_{3-4}$-cycloalkyl, $C_{2-4}$-alkenyl or $C_{2-4}$-alkynyl and $R^1$ is $C_{1-15}$-alkyl, $C_{2-15}$-alkenyl, $C_{2-15}$-alkynyl, $C_{3-7}$-cycloalkyl, $C_{4-8}$-cycloalkylalkyl, phenoxy, benzyloxy, morpholino, $C_{1-6}$-alkyl substituted piperidino, halogen, amino, $C_{1-6}$-acylamino, $C_{1-15}$-alkylamino, $C_{1-15}$-dialkylamino, $C_{1-15}$-alkoxyamino, S-$R^2$ or O—$R^2$ wherein $R^2$ is straight or branched $C_{1-15}$-alkyl, straight or branched $C_{2-15}$-alkenyl, straight or branched $C_{2-15}$-alkynyl, $R^3$—O—$R^4$, $R^3$—NH—$R^4$, $R^3$—S—$R^4$, $R^3$—O—$R^4$—O—$R^5$ wherein $R^3$, $R^4$ and $R^5$ independently are $C_{1-15}$-alkyl, $C_{2-15}$-alkenyl, $C_{2-15}$-alkynyl or a salt thereof with a pharmaceutically-acceptable acid.

All of the below shown structures are known to have affinity for the muscarinic receptors, but only the 3-alkyl-1,2,4-oxadiazol-5-yls (III and VII) and the 3-alkyl-1,2,4-thiadiazol-5-yls (IV and VIII) are agonists. The 5-alkyl-1,2,4-oxadiazol-3-yls (V and IX) and the 5-alkyl-1,2,4-thiadiazol-3-yls (VI and X) are antagonists.

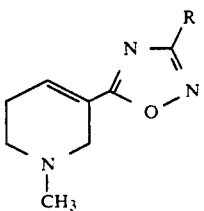
III

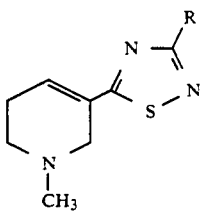
IV

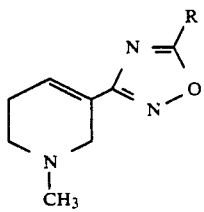
V

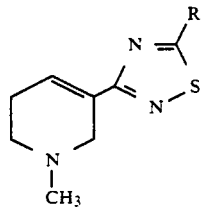
VI (wherein R = $C_{1-2}$-alkyl)

A common feature for all of the shown heterocycles with affinity for muscarinic receptors is that the substituent (R) always is in the beta position relative to the cyclic amine:

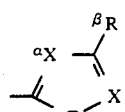
(XI)

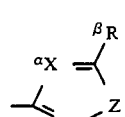
(XII)

X = C or N
Z = O or S

The difference between XI and XII is in the electronic distribution in the heterocycle. In other words, in XI the double bonds are in another relative position to the substituent than in XII.

Without wishing to be bound by any theory or mechanism it is believed that this is probably why structures with the general structure XI are muscarinic agonists and structures with the general structure XII are muscarinic antagonists.

It is therefore very surprising that heterocycles with a substituent in the alpha position to the cyclic amine as with the active compounds disclosed and claimed herein are extremely effective ester isosters. There are no known alpha-substituted heterocycles being ester isosters.

For instance, 3-(3-subst.-1,2,5-thiadiazol-4-yl)-1,2,5,6-tetrahydro-1-methylpyridines (XIII) have been found to be very potent muscarinic agonists with a better $M_1$-selectivity than agonists with the substituent in the beta position.

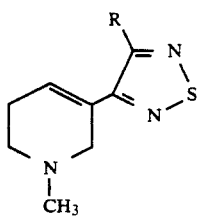

(XIII)

Furthermore, not all alpha-substituted heterocycles are ester isosters. It is believed that the position of the double bonds relative to the substituent (R) is very important. If the electrostatic properties are different from the one indicated in the heterocycle of structure XIII, the muscarinic agonist activity decreases dramatically. Compounds with the general formula XIV are either antagonists or inactive.

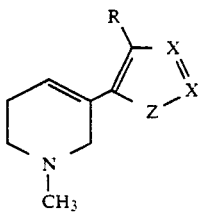

(XIV)

X = C or N
Z = O or S

The heterocycles with the general formula XV are, therefore, both structurally and biologically different from the general structures XI, XII and XIV.

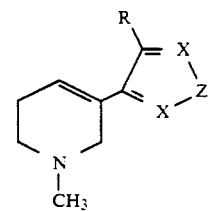

(XV)

X = C or N
Z = O or S

That the compounds XIII fit the muscarinic receptors better than the structures III to X is reflected in the fact that the substituent (R) is allowed to be bigger and more lipophilic without losing affinity and agonist activity. In fact, it is the $C_{4-8}$-alkoxy that show the best $M_1$-selectivity.

The pharmacological properties of the compounds of the present invention (Formula I) can be illustrated by determining their capability to inhibit the specific binding of $^3$H-Oxotremorine-M ($^3$H-Oxo)

$^3$H-Oxo labels muscarinic receptors in the CNS (with a preference for agonist domaines of the receptors). Three different sites are labelled by $^3$H-Oxo. These sites have affinity of 1.0, 20 and 3000 nM, respectively. Using the present experimental conditions only the high and medium affinity sites are determined. The inhibitory effects of compounds on $^3$H-Oxo binding reflects the affinity for muscarinic acetylcholine receptors.

All preparations are performed at 0°–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer is rinsed with 10 ml of buffer and the combined suspension centrifuged for 15 min at 40,000×g. The pellet is washed three times with buffer. In each step the pellet is homogenized as before in 2×10 ml of buffer and centrifuged for 10 min at 40,000×g. The final pellet is homogenized in 20 mM Hepes pH: 7.4 (100 ml per g of original tissue) and used for binding assay. Aliquots of 0.5 ml is added 25 µl of test solution and 25 µl of $^3$H-Oxotremorine (1.0 nM, final concentration) mixed and incubated for 30 min at 25° C. Non-specific binding is determined in triplicate using Arecoline (1 µg/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non-specific binding. Test substances are dissolved in 10 ml water (if necessary heated on a steambath for less than 5 minutes) at a concentration of 2.2 mg/ml. 25–75% inhibition of specific binding must be obtained before calculation of $IC_{50}$.

The test value will be given as $IC_{50}$ (the concentration (ng/ml) of the test substance which inhibits the specific binding of $^3$H-Oxo by 50%).

$$IC_{50} = (\text{applied test substance conc.}) \times \frac{1}{\left[\frac{C_o}{C_x} - 1\right]} \text{ ng/ml}$$

where $C_o$ is specific binding in control assays and $C_x$ is the specific binding in the test assay. (The calculations assume normal mass-action kinetics).

Test results obtained by testing some compounds of the present invention will appear from the following Table 1.

TABLE 1

| Compound No. | Inhibition in vitro OXO BINDING (ng/ml) |
|---|---|
| 1 | 1.5 |
| 2 | 0.4 |
| 3 | 0.2 |
| 4 | 0.5 |
| 5 | 3.5 |
| 6 | 1.9 |
| 7 | 1.7 |
| 8 | 1.9 |
| 9 | 3.6 |
| 10 | 2.3 |
| 11 | 0.9 |
| 12 | 0.3 |
| 13 | 0.3 |
| 14 | 0.4 |
| 15 | 0.6 |
| 16 | 3.3 |
| 17 | 19.0 |
| 18 | 3.6 |
| 19 | 92 |
| 20 | 5.9 |
| 21 | 2.4 |
| 22 | 0.4 |
| 23 | 0.3 |
| 24 | 0.4 |
| 25 | 12 |
| 26 | 0.4 |
| 27 | 0.8 |

TABLE 1-continued

| Compound No. | Inhibition in vitro OXO BINDING (ng/ml) |
|---|---|
| 28 | 1.3 |
| 29 | 0.6 |
| 30 | 0.4 |
| 31 | 0.7 |
| 32 | 1.4 |
| 33 | 1.0 |
| 34 | 1.0 |
| 35 | 0.6 |
| 36 | 0.3 |
| 37 | 6.3 |
| 38 | 7.4 |
| 39 | 4.1 |
| 40 | 3.7 |
| 41 | 1.3 |
| 42 | 7.0 |
| 43 | 4.0 |
| 44 | 14 |
| 45 | 115 |
| 46 | 18 |
| 47 | 0.3 |
| 48 | 0.6 |
| 49 | 0.7 |
| 50 | 300 |
| 51 | 300 |
| 52 | 65 |
| 53 | 1.2 |
| 54 | 20 |
| 55 | 8 |
| 56 | 2.1 |
| 57 | — |
| 58 | 50 |
| 59 | — |
| 60 | 164 |
| 61 | 50 |
| 62 | 32 |
| 63 | 25 |
| 64 | 58 |
| 65 | 0.6 |
| 66 | 1.8 |
| 67 | 1.6 |

The compounds of the present invention, together with a conventional adjuvant, carrier, or diluent, and if desired in the form of a pharmaceutically-acceptable acid addition salt thereof, may be placed in the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylase, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 1–100 mg in a pharmaceutically acceptable carrier per unit dosage.

The dosage of the compounds according to this invention is 1–100 mg/day, preferably 10–70 mg/day, when administered to patients, e.g. humans, as a drug.

A typical tablet which may be prepared by conventional tabletting techniques contains:

| | |
|---|---|
| Active compound | 5.0 mg |
| Lactosum | 67.8 mg Ph.Eur. |
| Avicel ® | 31.5 mg |
| Amberlite ® | 1.0 |
| Magnesii stearas | 0.25 mg Ph.Eur. |

Due to the high muscarinic cholinergic receptor agonistic activity, the compounds of the invention are extremely useful in the treatment of symptoms related to a reduction of the cognitive functions of the brain of mammals, when administered in an amount effective for stimulating the cognitive functions of the forebrain and hippocampus. The important stimulating activity of the compounds of the invention includes both activity against the pathophysiological disease, Alzlheimer's disease, as well as against normal degeneration of brain function.

The compounds of the invention may accordingly be administered to a subject, e.g., a living animal body, including a human, in need of stimulation of the cognitive functions of the forebrain and hippocampus, and if desired in the form of a pharmaceutically-acceptable acid addition salt thereof (such as hydrobromide, hydrochloride, or sulfate, in any event prepared in the usual or conventional manner, e.g. evaporation to dryness of the free base in solution together with the acid), ordinarily concurrently, simultaneously, or together with a pharmaceutically-acceptable carrier or diluent, especially and preferably in the form of a pharmaceutical composition thereof, whereof by oral, rectal, or parenteral (including subcutaneous) route, in an effective forebrain and hippocampus stimulating amount, and in any event an amount which is effective for improving the cognitive function of mammals due to their muscarinic cholinergic receptor agonistic activity.

The compounds of this invention are also useful analgesic agents and therefore useful in the treatment of severe painful conditions.

Furthermore, the compounds of this invention are useful in the treatment of glaucoma.

Suitable dosage ranges are 1-100 milligrams daily, 10-100 milligrams daily, and especially 30-70 milligrams daily, depending as usual upon the exact mode of administration, form in which administered, the indication toward which the administration is directed, the subject involved and the body weight of the subject involved, and the preference and experience of the physician or veterinarian in charge.

The preferred methods for the preparation of the active compounds of this invention are illustrated in the following examples in more detail.

EXAMPLE 1

A. 3-(4-chloro-1,2,5-thiadiazol-3-yl)pyridine

To a solution of sulfurmonochloride (2.4 ml, 30 mmol) in N,N-dimethylformamide (5 ml) was slowly added alpha-aminoalpha(3-pyridyl)acetonitril (Archive der Pharmazie 289 (4) (1956)) (1.70 g, 10 mmol). The reaction mixture was stirred at room temperature for 18 h. Water (20 ml) was added and the aqueous phase was extracted with ether and the ether phase discharged. A 50% potassium hydroxide solution was added to the aqueous phase to pH>9. The aqueous phase was extracted several times with ether and the ether phases were dried and evaporated. The residue was purified by column chromatography (SiO$_2$, eluent: ethyl acetate/methylene chloride (1:1)). The title compound was collected in 45% (880 mg) yield. M+: 197

B. 3-(4-methoxy-1,2,5-thiadiazol-3-yl)pyridine

To a solution of sodium (460 mg, 20 mmol) in methanol (10 ml) was added 3-(4-chloro-1,2,5-thiadiazol-3-yl)pyridine (750 mg, 3.8 mmol). The mixture was stirred at 50° C. for 1 h and evaporated. The residue was dissolved in water and extracted with methylene chloride. The combined organic phases were dried and evaporated to give the title compound, which crystallized with petroleum ether in a 630 mg (86%) yield.

C. 3-(4-methoxy-1,2,5-thiadiazol-3-yl)-1-methyl-pyridinium iodide

A mixture of methyl iodide (0.37 ml, 6 mmol) and 3-(4-methoxy-1,2,5-thiadiazol-3-yl)pyridine (500 mg, 2.5 mmol) in acetone (10 ml) was stirred at room temperature for 18 h. The title compound precipitated from the solution and was collected by filtration. Yield: 1.0 g (100%).

D. 1,2,5,6-tetrahydro-3-(4-methoxy-1,2,5-thiadiazol-3-yl)-1-methylpyridine oxalate Sodium borohydride (460 mg, 12 mmol) was added to a solution of 3-(4-methoxy-1,2,5-thiadiazol-3-yl)-1-methylpyridinium iodide (1.0 g, 3 mmol) in ethanol (99.9%, 20 ml) and the reaction mixture was stirred at room temperature for 1 h. After evaporation the residue was dissolved in water and extracted with methylene chloride. The dried organic phases were evaporated and the residue purified by column chromatography (SiO$_2$, eluent: ethyl acetate/methanol (4:1)). The title compound was crystallized as the oxalate salt from acetone. Yield: 390 mg. (M.p. 150° C.; M+: 211; Compound 1).

EXAMPLE 2

A. 3-(4-ethoxy-1,2,5-thiadiazol-3-yl)pyridine

To a solution of sodium (440 mg, 17 mmol) in ethanol (10 ml) was added 3-(4-chloro-1,2,5-thiadiazol-3-yl)pyridine (540 mg, 3.3 mmol). The mixture was stirred at 40° C. for 10 h and evaporated. The residue was dissolved in water and extracted with methylene chloride. The combined organic phases were dried and evaporated to yield 520 mg (76%) of the title compound.

B. 3-(4-ethoxy-1,2,5-thiadiazol-3-yl)-1-methyl-pyridinium iodide

A mixture of methyl iodide (0.3 ml, 5 mmol) and 3-(4-ethoxy-1,2,5-thiadiazol-3-yl)pyridine (520 mg, 2.5 mmol) in acetone (10 ml) was stirred at room temperature for 18 h. The title compound precipitated from the solution and was collected by filtration to yield 0.72 g (83%).

C. 3-(4-ethoxy-1,2,5-thiadiazol-3-yl)-1,2,5,6-tetrahydro-1-methylpyridine oxalate Sodium borohydride (300 mg, 8 mmol) was added to a solution of 3-(4-ethoxy-1,2,5-thiadiazol-3-yl)-1-methylpyridinium iodide (0.72 g, 2 mmol) in ethanol (99.9%, 20 ml) and the reaction mixture was stirred at room temperature for 1 h. After evaporation the residue was dissolved in water and extracted with methylene chloride. The dried organic phases were evaporated and the residue purified by column chromatography (SiO$_2$, eluent: ethyl acetate/methanol (4:1)). The title compound was crystallized as the oxalate salt from acetone, and recrystallized from methanol to yield 190 mg. (M.p. 137° C.; M+: 225; Compound 2).

EXAMPLE 3

A. 3-(4-propoxy-1,2,5-thiadiazol-3-yl)pyridine

To a solution of sodium (440 mg, 17 mmol) in 1-propanol (10 ml) was added 3-(4-chloro-1,2,5-thiadiazol-3-yl)pyridine (650 mg, 3.3 mmol). The mixture was stirred at 50° C. for 2 h and evaporated. The residue was dissolved in water and extracted with methylene chloride. The combined organic phases were dried and evaporated to yield 700 mg (96%) of the title compound.

B. 3-(4-propoxy-1,2,5-thiadiazol-3-yl)-1-methylpyridinium iodide

A mixture of methyl iodide (0.37 ml, 6 mmol) and 3-(4-propoxy-1,2,5-thiadiazol-3-yl)pyridine (700 mg, 3.1 mmol) in acetone (10 ml) was stirred at room temperature for 18 h. The title compound precipitated from the solution and was collected by filtration to yield 0.98 g (88%).

C.
1,2,5,6-tetrahydro-1-methyl-3-(4-propoxy-1,2,5-thiadiazol-3-yl)pyridine oxalate Sodium borohydride (380 mg, 10 mmol) was added to a solution of 3-(4-propoxy-1,2,5-thiadiazol-3-yl)-1-methylpyridinium iodide (980 mg, 2.7 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography ($SiO_2$ eluent: ethyl acetate/methanol (4:1)). The title compound was crystallized as the oxalate salt from acetone to yield 440 mg. (M.p. 148° C.; $M^+$: 239; Compound 3).

EXAMPLE 4

A. 3-(4-butoxy-1,2,5-thiadiazol-3-yl)pyridine

To a solution of sodium (290 mg, 12.5 mmol) in n-butanol (10 ml) was added 3-(4-chloro-1,2,5-thiadiazol-3-yl)pyridine (490 mg, 2.5 mmol). The mixture was stirred at 25° C. for 18 h and evaporated. The residue was dissolved in water and extracted with methylene chloride. The combined organic phases were dried and evaporated to yield 580 mg (100%) of the title compound.

B.
3-(4-butoxy-1,2,5-thiadiazol-3-yl)-1-methylpyridinium iodide

A mixture of methyl iodide (0.3 ml, 5 mmol) and 3-(4-butoxyoxy-1,2,5-thiadiazol-3-yl)pyridine (580 mg, 2.5 mmol) in acetone (5 ml) was stirred at room temperature for 18 h. The title compound precipitated from the solution and was collected by filtration to yield 0.60 g (64%).

C
3-(4-butoxy-1,2,5-thiadiazol-3-yl)-1,2,5,6-tetrahydro-1-methylpyridine oxalate Sodium borohydride (240 mg, 6.4 mmol) was added to a solution of 3-(4-butoxy-1,2,5-thiadiazol-3-yl)-1-methylpyridinium iodide (0.60 g, 1.6 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography ($SiO_2$, eluent: ethyl acetate/methanol (4:1)). The title compound was crystallized as the oxalate salt from acetone to yield 280 mg. (M.p. 158° C.; $M^+$: 253; Compound 4).

EXAMPLE 5

A. 3-(4-isopropoxy-1,2,5-thiadiazol-3-yl)pyridine

To a solution of sodium (290 mg, 12.5 mmol) in isopropanol (10 ml) was added 3-(4-chloro-1,2,5-thiadiazol-3-yl)pyridine (490 mg, 2.5 mmol). The mixture was stirred at 25° C. for 18 h and evaporated. The residue was dissolved in water and extracted with ethyl acetate. The combined organic phases were dried and evaporated to yield 540 mg (98%) of the title compound.

B.
3-(4-isopropoxy-1,2,5-thiadiazol-3-yl)-1-methylpyridinium iodide

A mixture of methyl iodide (0.3 ml, 5 mmol) and 3-(4-isopropoxy-1,2,5-thiadiazol-3-yl)pyridine (540 mg, 2.4 mmol) in acetone (5 ml) was stirred at room temperature for 18 h. The title compound precipitated from the solution and was collected by filtration to yield 0.68 g (77%).

C.
1,2,5,6-tetrahydro-3-(4-isopropoxy-1,2,5-thiadiazol-3-yl)-1-methylpyridine oxalate Sodium borohydride (280 mg, 7.2 mmol) was added to a solution of 3-(4-isopropoxy-1,2,5-thiadiazol-3-yl)-1-methylpyridinium iodide (650 mg, 1.8 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography ($SiO_2$, eluent: ethyl acetate/methanol (4:1)). The title compound was crystallized as the oxalate salt from acetone to yield 280 mg. (M.p. 164° C.; ..$M^+$: 239; Compound 5).

EXAMPLE 6

A. 3-(4-pentyloxy-1,2,5-thiadiazol-3-yl)pyridine

To a solution of sodium (230 mg, 10 mmol) in 1-pentanol (20 ml) was added 3-(4-chloro-1,2,5-thiadiazol-3-yl)pyridine (490 mg, 2.5 mmol). The mixture was stirred at 50° C. for 3 h and evaporated. The residue was dissolved in water and extracted with methylene chloride. The combined organic phases were dried and evaporated to give the wanted compound.

B.
3-(4-pentyloxy-1,2,5-thiadiazol-3-yl)-1-methylpyridinium iodide

A mixture of methyl iodide (0.3 ml, 5 mmol) and 3-(4-pentyloxy-1,2,5-thiadiazol-3-yl) pyridine (620 mg, 2.5 mmol) in acetone (5 ml) was stirred at room temperature for 18 h. The title compound precipitated from the solution and was collected by filtration to yield 0.81 g (84%).

C.
1,2,5,6-tetrahydro-1-methyl-3-(4-pentyloxy-1,2,5-thiadiazol-3-yl)pyridine oxalate Sodium borohydride (300 mg, 8 mmol) was added to a solution of 3-(4-pentyloxy-1,2,5-thiadiazol-3-yl)-1-methylpyridinium iodide (0.81 g, 2 mmol) in ethanol (99.9%, 20 ml) and the reaction mixture was stirred at 0° C. for 1 h. After evaporation the residue was dissolved in water and extracted with ether. The dried organic phases were evaporated and the residue purified by column chromatography ($SiO_2$, eluent: ethyl acetate/methanol (4:1)). The title compound was crystallized as the oxalate salt from acetone, and recrystallized from methanol to yield 220 mg. (M.p. 150° C.; $M^+$: 267; Compound 6).

EXAMPLE 7

A. 3-(4-isobutoxy-1,2,5-thiadiazol-3-yl)pyridine

To a solution of sodium (230 mg, 10 mmol) in isobutanol (10 ml) was added 3-(4-chloro-1,2,5-thiadiazol-3-yl)pyridine (490 mg, 2.5 mmol). The mixture was stirred at 50° C. for 3 h and evaporated. The residue was dissolved in water and extracted with methylene chloride. The combined organic phases were dried and evaporated to give the wanted compound.

B.
3-(4-isobutoxy-1,2,5-thiadiazol-3-yl)-1-methyl-pyridinium iodide

A mixture of methyl iodide (0.6 ml, 10 mmol) and 3-(4-isobutoxy-1,2,5-thiadiazol-3-yl)pyridine (588 mg, 2.5 mmol) in acetone (5 ml) was stirred at room temperature for 18 h. The title compound precipitated from the solution and was collected by filtration to yield 0.88 (87%).

C.
1,2,5,6-tetrahydro-3-(4-isobutoxy-1,2,5-thiadiazol-3-yl)-1-methylpyridine oxalate Sodium borohydride (160 mg, 4.3 mmol) was added to a solution of 3-(4-isobutoxy-1,2,5-thiadiazol-3-yl)-1-methylpyridinium iodide (0.82 g, 2.2 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography ($SiO_2$, eluent: ethyl acetate/methanol (4:1)). The title compound was crystallized as the oxalate salt from acetone to yield 400 mg. (M.p. 135° C.; $M^+$: 253; Compound 7).

EXAMPLE 8
A. 3-(4-isopentyloxy-1,2,5-thiadiazol-3-yl)pyridine

To a solution of sodium (230 mg, 10 mmol) in isopentanol (20 ml) was added 3-(4-chloro-1,2,5-thiadiazol-3-yl)pyridine (490 mg, 2.5 mmol). The mixture was stirred at 50° C. for 2 h and evaporated. The residue was dissolved in water and extracted with ether. The combined organic phases were dried and evaporated to give the wanted compound.

B.
3-(4-isopentyloxy-1,2,5-thiadiazol-3-yl)-1-methyl-pyridinium iodide

A mixture of methyl iodide (0.5 ml, 10 mmol) and 3-(4-isopentyloxy-1,2,5-thiadiazol-3-yl)pyridine (622 mg, 2.5 mmol) in acetone (5 ml) was stirred at room temperature for 18 h. The title compound precipitated from the solution and was collected by filtration to yield 0.78 g (81%).

C.
1,2,5,6-tetrahydro-3-(4-isopentyloxy-1,2,5-thiadiazol-3-yl)-1-methylpyridine oxalate Sodium borohydride (150 mg, 4 mmol) was added to a solution of 3-(4-isopentyloxy-1,2,5-thiadiazol-3-yl)-1-methylpyridinium iodide (780 mg, 2 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography ($SiO_2$, eluent: ethyl acetate/methanol (4:1)). The title compound was crystallized as the oxalate salt from acetone to yield 350 mg. (M.p. 152° C.; $M^+$: 267; Compound 8).

EXAMPLE 9
A. 3-(4-hexyloxy-1,2,5-thiadiazol-3-yl)pyridine

To a solution of sodium (230 mg, 10 mmol) in 1-hexanol (15 ml) was added 3-(4-chloro-1,2,5-thiadiazol-3-yl)pyridine (490 mg, 2.5 mmol). The mixture was stirred at 50° C. for 2 h and evaporated. The residue was dissolved in water and extracted with ether. The combined organic phases were dried and evaporated to give the wanted compound.

B.
3-(4-hexyloxy-1,2,5-thiadiazol-3-yl)-1-methyl-pyridinium iodide

A mixture of methyl iodide (0.5 ml, 7.5 mmol) and 3-(4-hexyloxy-1,2,5-thiadiazol-3-yl)pyridine (658 mg, 2.5 mmol) in acetone (5 ml) was stirred at room temperature for 18 h. The title compound precipitated from the solution and was collected by filtration to yield 0.81 g (80%).

C.
3-(4-hexyloxy-1,2,5-thiadiazol-3-yl)-1,2,5,6-tetrahydro-1-methylpyridine oxalate Sodium borohydride (230 mg, 6 mmol) was added to a solution of 3-(4-hexyloxy-1,2,5-thiadiazol-3-yl)-1-methylpyridinium iodide (810 mg, 2 mmol) in ethanol (99.9%, 20 ml) and the reaction mixture was stirred at room temperature for 1 h. After evaporation the residue was dissolved in water and extracted with ethyl acetate. The dried organic phases were evaporated and the residue purified by column chromatography ($SiO_2$, eluent: ethyl acetate/methanol (4:1)). The title compound was crystallized as the oxalate salt from acetone to yield 350 mg. (M.p. 148° C.; $M^+$: 281; Compound 9).

EXAMPLE 10
A. 3-(4-benzyloxy-1,2,5-thiadiazol-3-yl)pyridine

To a solution of sodium (490 mg, 2.5 mmol) in benzyl alcohol (15 ml) was added 3-(4-chloro-1,2,5-thiadiazol-3-yl)pyridine (490 mg, 2.5 mmol). The mixture was stirred at 50° C. for 2 h and evaporated. The residue was dissolved in water and extracted with ether. The combined organic phases were dried and evaporated to give the wanted compound.

B.
3-(4-benzyloxy-1,2,5-thiadiazol-3-yl)-1-methyl-pyridinium iodide

A mixture of methyl iodide (0.5 ml, 7.5 mmol) and 3-(4-benzyloxy-1,2,5-thiadiazol-3-yl)pyridine (673 mg, 2.5 mmol) in acetone (5 ml) was stirred at room temperature for 18 h. The title compound precipitated from the solution and was collected by filtration to yield 0.75 g (73%).

C.
3-(4-benzyloxy-1,2,5-thiadiazol-3-yl)-1,2,5,6-tetrahydro-1-methylpyridine oxalate Sodium borohydride (230 mg, 6 mmol) was added to a solution of 3-(4-benzyloxy-1,2,5-thiadiazol-3-yl)-1-methylpyridinium iodide (750 mg, 1.8 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatographya ($SiO_2$, eluent: ethyl acetate/methanol (4:1)). The title compound was crystallized as the oxalate salt from acetone to yield 340 mg. (M.p. 149° C.; $M^+$: 287; Compound 10).

EXAMPLE 11

A. 3-(4-(3-butenyloxy-1,2,5-thiadiazol-3-yl)pyridine

To a solution of 3-buten-1-ol (540 mg, 7.5 mmol) and sodium hydride (180 mg, 7.5 mmol) in dry tetrahydrofuran was added a solution of 3-(4-chloro-1,2,5-thiadiazol-3-y-1)pyridine (490 mg, 2.5 mmol) in dry tetrahydrofuran. The reaction mixture was stirred at room temperature for 1 h. Water was added and the mixture was extracted with ether. The ether phase was dried and evaporated to yield 650 mg of the title compound.

B. 3-(4-(3-butenyloxy)-1,2,5-thiadiazol-3-yl)-1-methylpyridinium iodide

A mixture of methyl iodide (0.5 ml, 7.5 mmol) and 3-(4-(3-butenyloxy)-1,2,5-thiadiazol-3-yl) pyridine (583 mg, 2.5 mmol) in acetone (5 ml) was stirred at room temperature for 18 h. The title compound precipitated from the solution and was collected by filtration to yield 890 mg (96%).

C. 3-(4-(3-butenyloxy)-1,2,5-thiadiazol-3-yl)-1,2,5,6-tetrahydro-1-methylpyridine oxalate Sodium borohydride (210 mg, 5.5 mmol) was added to a solution of 3-(4-(3-butenyloxy-1,2,5-thiadiazol-3-yl)-1-methylpyridinium iodide (1.03 g, 2.8 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 380 mg. (M.p. 141° C.; M+: 251; Compound 11).

EXAMPLE 12

A. 3-(4-(2-butynyloxy)-1,2,5-thiadiazol-3-yl)pyridine

To a solution of 2-butyn-1-ol (530 mg, 7.5 mmol) and sodiumhydride (180 mg, 7.5 mmol) in dry tetrahydrofuran was added a solution of 3-(4-chloro-1,2,5-thiadiazol-3-yl)pyridine (490 mg, 2.5 mmol) in dry tetrahydrofuran. The reaction mixture was stirred at room temperature for 2 h. Water was added and the mixture was extracted with ether. The ether phase was dried and evaporated to give the title compound.

B. 3-(4-(2-butynyloxy)-1,2,5-thiadiazol-3-yl)-1-methylpyridinium iodide

A mixture of methyl iodide (0.5 ml, 7.5 mmol) and 3-(4-(2-butynyloxy)-1,2,5-thiadiazol-3-yl) pyridine (578 mg, 2.5 mmol) in acetone (5 ml) was stirred at room temperature for 18 h. The title compound precipitated from the solution and was collected by filtration to yield 0.88 g (95%).

C. 3-(4-(2-butynyloxy)-1,2,5-thiadiazol-3-yl)-1,2,5,6-tetrahydro-1-methylpyridine oxalate Sodium borohydride (180 mg, 4.7 mmol) was added to a solution of 3-(4-(2-butynyloxy)-1,2,5-thiadiazol-3-yl)-1-methylpyridinium iodide (0.88 g, 2.35 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone, and recrystallized in methanol to yield 140 mg. (M.p. 158° C.; M+: 249; Compound 12).

EXAMPLE 13

A. 3-(4-propargyloxy-1,2,5-thiadiazol-3-yl)pyridine

To a solution of propargyl alcohol (420 mg, 7.5 mmol) and sodium hydride (180 mg, 7.5 mmol) in dry tetrahydrofuran was added a solution of 3-(4-chloro-1,2,5-thiadiazol-3-yl)pyridine (490 mg, 2.5 mmol) in dry tetrahydrofuran. The reaction mixture was stirred at room temperature for 2 h. Water was added and the mixture was extracted with ether. The ether phase was dried and evaporated to yield 530 mg (98%) of the title compound.

B. 3-(4-propargyloxy-1,2,5-thiadiazol-3-yl)-1-methylpyridinium iodide

A mixture of methyl iodide (0.45 ml, 7.2 mmol) and 3-(4-propargyloxy-1,2,5-thiadiazol-3-yl) pyridine (430 mg, 2.4 mmol) in acetone (5 ml) was stirred at room temperature for 18 h. The title compound precipitated from the solution and was collected by filtration to yield 0.58 g (67%).

C. 1,2,5,6-tetrahydro-1-methyl-3-(4-propargyloxy-1,2,5-thiadiazol-3-yl)pyridine oxalate Sodium borohydride (230 mg, 6 mmol) was added to a solution of 3-(4-propargyloxy-1,2,5-thiadiazol-3-yl)-1-methylpyridinium iodide (0.68 g, 1.9 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 200 mg. (M.p. 155° C.; M+: 235; Compound 13).

EXAMPLE 14

A. 3-(4-cyclopropylmethoxy-1,2,5-thiadiazol-3-yl)pyridine

To a solution of cyclopropylcarbinol (360 mg, 5 mmol) and sodium hydride (110 mg, 5 mmol) in dry tetrahydrofuran was added a solution of 3-(4-chloro-1,2,5-thiadiazol-3-yl)pyridine (490 mg, 2.5 mmol) in dry tetrahydrofuran. The reaction mixture was stirred at room temperature for 3 h. Water was added and the mixture was extracted with ether. The ether phase was dried and evaporated to yield 400 mg (69%) of the title compound.

B. 3-(4-cyclopropylmethoxy-1,2,5-thiadiazol-3-yl)-1-methylpyridinium iodide

A mixture of methyl iodide (0.25 ml, 4 mmol) and 3-(4-cyclopropylmethoxy-1,2,5-thiadiazol-3-yl) pyridine (400 mg, 1.7 mmol) in acetone (5 ml) was stirred at room temperature for 36 h. The title compound precipitated from the solution and was collected by filtration to yield 0.41 g (65%).

C.
3-(4-cyclopropylmethoxy-1,2,5-thiadiazol-3-yl)-1,2,5,6-tetrahydro-1-methylpyridine oxalate Sodium borohydride (170 mg, 4.4 mmol) was added to a solution of 3-(4-cyclopropylmethoxy-1,2,5-thiadiazol-3-yl)-1-methylpyridinium iodide (410 mg, 1.1 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 130 mg. (M.p. 153° C.; M+: 251; Compound 14).

EXAMPLE 15

A.
3-(4-chloro-1,2,5-thiadiazol-3-yl)-1-methylpyridinium iodide

A solution of 3-(4-chloro-1,2,5-thiadiazol-3-yl)pyridine (1.98 g, 10 mmol) and methyl iodide (4.25 g, 30 mmol) in acetone (10 ml) was stirred at room temperature for 16 h. The precipitate was collected by filtration to yield 3.40 g (100%) of the title compound.

B.
3-(4-chloro-1,2,5-thiadiazol-3-yl)-1,2,5,6-tetrahydro-1-methylpyridine oxalate To a suspension of sodium borohydride (330 mg, 8.6 mmol) in ethanol (20 ml) was added 3-(4-chloro-1,2,5-thiadiazol-3-yl)-1-methylpyridinium iodide (1.46 g, 4.3 mmol) at 0° C. The reaction mixture was stirred for 1 h at 0° C. Water was added and the mixture was extracted with ethyl acetate. After drying, the ethyl acetate phase was evaporated and the residue purified by column chromatography (eluent: ethyl acetate: methanol (4:1)). Yield: 880 mg (95%). Crystallization with oxalic acid from acetone gave the title compound. (M.p. 124° C.; M+: 215 and 217; Compound 16).

C.
1,2,5,6-tetrahydro-3-(4-methoxyethoxy-1,2,5-thiadiazol-3-yl)-1-methylpyridine oxalate To a solution of sodium (120 mg, 5 mmol) in 2-methoxyethanol (10 ml) was added 3-(4-chloro-1,2,5-thiadiazol-3-yl)-1,2,5,6-tetrahydro-1-methylpyridine oxalate (310 mg, 1 mmol). The mixture was stirred at 50° C. for 18 h and evaporated. The residue was dissolved in water and extracted with ethyl acetate. The combined organic phases were dried and evaporated. The title compound was crystallized as the oxalate salt from acetone to yield 270 mg. (M.p. 152.1° C.; M+: 253; Compound 15).

D.
3-(4-chloro-1,2,5-thiadiazol-3-yl)-1,2,5,6-tetrahydropyridine hydrochloride

To a solution of 3-(4-chloro-1,2,5-thiadiazol-3-yl)-1,2,5,6-tetrahydro-1-methylpyridine (670 mg, 3.1 mmol) in 1,2-dichloroethane (20 ml) was added a solution of 1-chloromethyl-chloroformate (440 mg, 3.1 mmol) in 1,2-dichloroethane at 0° C. The reaction mixture was heated to 40° C. for 2 h and evaporated. The residue was dissolved in methanol and heated to reflux for 1 h. After cooling to room temperature the precipitate was collected by filtration to yield 320 mg (41%). (M.p. 224° C.; M+: 201 and 203; Compound 17).

E.
3-(4-butoxy-1,2,5-thiadiazol-3-yl)-1,2,5,6-tetrahydropyridine oxalate

To a solution of sodium (150 mg, 6.5 mmol) in 1-butanol (15 ml) was added 3-(4-chloro-1,2,5-thiadiazol-3-yl)-1,2,5,6-tetrahydropyridine hydrochloride (240 mg, 1 mmol). The reaction mixture was stirred at 50° C. for 1 h. After evaporation the residue was dissolved in water and extracted with ethyl acetate. The ethyl acetate phase was dried and evaporated to give an oil (200 mg). Crystallization as the oxalate salt from acetone gave the title compound. Yield: 170 mg (52%). (M.p. 173°–174° C.; M+: 239; Compound 18).

EXAMPLE 16

A. 3-(4-chloro-1,2,5-thiadiazol-3-yl)-1-ethylpyridinium iodide

A solution of 3-(4-chloro-1,2,5-thiadiazol-3-yl)pyridine (1.13 g, 5.7 mmol) and ethyl iodide (22.65 g, 17 mmol) in acetone (15 ml) was stirred at 40° C. for 16 h. The precipitate was collected by filtration giving the title compound. Yield: 510 mg (26%).

B.
3-(4-chloro-1,2,5-thiadiazol-3-yl)-1-ethyl-1,2,5,6-tetrahydropyridine oxalate To a suspension of sodium borohydride (170 mg, 4.5 mmol) in ethanol (10 ml) was added 3-(4-chloro-1,2,5-thiadiazol-3-yl)-1-ethylpyridinium iodide (510 mg, 1.5 mmol) at 0° C. The mixture was stirred for 1 h at 0° C. Water was added and the mixture was extracted with ethyl acetate. After drying, the ethyl acetate phase was evaporated and the residue purified by column chromatography (eluent: ethyl acetate/methanol (4:1)). Crystallization with oxalic acid from acetone gave the title compound to yield 70 mg. (M.p. 143° C.; M+: 229 and 231; Compound 19).

EXAMPLE 17

A. 3-(4-ethoxy-1,2,5-thiadiazol-3-yl)-1-ethylpyridinium iodide

A solution of 3-(4-ethoxy-1,2,5-thiadiazol-3-yl)pyridine (0.90 g, 4.3 mmol) and ethyl iodide (2.03 g, 13 mmol) in acetone (4 ml) was stirred at 40° C. for 16 h. The precipitate was collected by filtration giving the title compound to yield 1.34 g (86%).

B.
3-(4-ethoxy-1,2,5-thiadiazol-3-yl)-1-ethyl-1,2,5,6-tetrahydropyridine oxalate To a suspension of sodium borohydride (410 mg, 10.8 mmol) in ethanol (10 ml) was added 3-(4-ethoxy-1,2,5-thiadiazol-3-yl)-1-ethylpyridinium iodide (1.32 g, 3.6 mmol) at 0° C. The mixture was stirred for 1 h at 0° C. Water was added and the mixture was extracted with ethyl acetate. After drying, the ethyl acetate phase was evaporated and the residue purified by column chromatography (eluent: ethyl acetate/methanol (4:1)). Crystallization with oxalic acid from acetone gave a yield of 0.49 g of the title compound. (M.p. 120°–122° C.; M+: 239; Compound 20).

EXAMPLE 18

3-(4-heptyloxy-1,2,5-thiadiazol-3-yl)-1,2,5,6-tetrahydro-1-methylpyridine oxalate To a solution of sodium (120 mg, 5 mmol) in 1-heptanol (10 ml) was added 3-(4-chloro-1,2,5-thiadiazol-3-yl)-1,2,5,6-tetrahydro-1-methylpyridine oxalate (310 mg, 1 mmol). The reaction mixture was stirred at 50° C. for 18 h. After evaporation the residue was dissolved in water and extracted with ethyl acetate. The ethyl acetate phase was dried and evaporated to give an oil. Crystallization as the oxalate salt from acetone gave the title compound. Yield: 270 mg (70%). (M.p. 152° C.; M+: 295; Compound 21).

EXAMPLE 19

A. 3-(4-(3-pentynyloxy)-1,2,5-thiadiazol-3-yl)pyridine

To a solution of 3-pentyn-1-ol (750 mg, 9 mmol) and sodium hydride (310 mg, 9 mmol) in dry tetrahydrofuran was added a solution of 3-(4-chloro-1,2,5-thiadiazol-3-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B.
3-(4-(3-pentynyloxy)-1,2,5-thiadiazol-3-yl)-1-methylpyridinium iodide

A mixture of methyl iodide (0.6 ml, 9 mmol) and 3-(4-(3-pentynyloxy)-1,2,5-thiadiazol-3-yl) pyridine (3 mmol) in acetone (10 ml) was stirred at room temperature for 18 h. The title compound precipitated from the solution and was collected by filtration to yield 0.68 g (59%).

C.
3-(4-(3-pentynyloxy)-1,2,5-thiadiazol-3-yl)-1,2,5,6-tetrahydro-1-methylpyridine oxalate Sodium borohydride (150 mg, 4 mmol) was added to a solution of 3-(4-(3-pentynyloxy)-1,2,5-thiadiazol-3-yl)-1-methylpyridinium iodide (0.68 g, 1.7 mmol) in ethanol (99.9%, 15 ml) and the reaction mixture was stirred at −10° C. for 1 h. After evaporation the residue was dissolved in water and extracted with ethyl acetate. The dried organic phases were evaporated and the residue purified by column chromatography (SiO2, eluent: ethyl acetate/methanol (4:1)). The title compound was crystallized as the oxalate salt from acetone to yield 240 mg. (M.p. 166°-167° C.; M+: 263; Compound 22).

EXAMPLE 20

A. 3-(4-(4-pentenyloxy)-1,2,5-thiadiazol-3-yl)pyridine

To a solution of 4-penten-1-ol (640 mg, 7.5 mmol) and sodium hydride (260 mg, 7.5 mmol) in dry tetrahydrofuran was added a solution of 3-(4-chloro-1,2,5-thiadiazol-3-yl)pyridine (490 mg, 2.5 mmol) in dry tetrahydrofuran. The reaction mixture was stirred at room temperature for 1 h. Water was added and the mixture was extracted with ether. The ether phase was dried and evaporated to give the title compound.

B.
3-(4-(4-pentenyloxy)-1,2,5-thiadiazol-3-yl)-1-methylpyridinium iodide

A mixture of methyl iodide (0.5 ml, 7.5 mmol) and 3-(4-(4-pentenyloxy)-1,2,5-thiadiazol-3-yl) pyridine (2.5 mmol) in acetone (10 ml) was stirred at room temperature for 18 h. The title compound precipitated from the solution and was collected by filtration to yield 0.67 g (69%).

C.
3-(4-(4-pentenyloxy)-1,2,5-thiadiazol-3-yl)-1,2,5,6-tetrahydro-1-methylpyridine oxalate Sodium borohydride (150 mg, 4 mmol) was added to a solution of 3-(4-(4-pentenyloxy)-1,2,5-thiadiazol-3-yl)-1-methylpyridinium iodide (0.67 g, 1.7 mmol) in ethanol (99.9%, 15 ml) and the reaction mixture was stirred at −10° C. for 1 h. After evaporation the residue was dissolved in water and extracted with ethyl acetate. The dried organic phases were evaporated and the residue purified by column chromatography (SiO2, eluent: ethyl acetate/methanol (4:1)). The title compound was crystallized as the oxalate salt from acetone to yield 150 mg. (M.p. 141°-142° C.; M+: 265; Compound 23).

EXAMPLE 21

A. 3-(4-(2-propenyloxy)-1,2,5-thiadiazol-3-yl)pyridine

To a solution of allyl alcohol (650 mg, 9 mmol) and sodium hydride (310 mg, 9 mmol) in dry tetrahydrofuran was added a solution of 3-(4-chloro-1,2,5-thiadiazol-3-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B.
3-(4-(2-propenyloxy)-1,2,5-thiadiazol-3-yl)-1-methylpyridinium iodide

A mixture of methyl iodide (0.4 ml, 6 mmol) and 3-(4-(2-propenyloxy)-1,2,5-thiadiazol-3-yl) pyridine (3 mmol) in acetone (5 ml) was stirred at room temperature for 18 h. The title compound precipitiated from the solution and was collected by filtration to give 0.96 g (88%).

C.
3-(4-(2-propenyloxy)-1,2,5-thiadiazol-3-yl)-1,2,5,6-tetrahydro-1-methylpyridine oxalate Sodium borohydride (210 mg, 5.5 mmol) was added to a solution of 3-(4-(2-propenyloxy)-1,2,5-thiadiazol-3-yl)-1-methylpyridinium iodide (0.96 g, 2.6 mmol) in ethanol (99.9%, 25 ml) and the reaction mixture was stirred at −10° C. for 1 h. After evaporation the residue was dissolved in water and extracted with ethyl acetate. The dried organic phases were evaporated and the residue purified by column chromatography (SiO2, eluent: ethyl acetate/methanol (4:1)). The title compound was crystallized as the oxalate salt from acetone to yield 270 mg. (M.p. 136°-137° C.; M+: 237; Compound 24).

EXAMPLE 22

A. 3-(4-octyloxy-1,2,5-thiadiazol-3-yl)pyridine

To a solution of sodium (350 mg, 15 mmol) in 1-octanol (10 ml) was added 3-(4-chloro-1,2,5-thiadiazol-3-yl)pyridine (590 mg, 3 mmol). The mixture was stirred at 50° C. for 1 h and evaporated. The residue was dissolved in water and extracted with methylene chloride. The combined organic phases were dried and evaporated to give the title compound.

B. 3-(4-octyloxy-1,2,5-thiadiazol-3-yl)-1-methylpyridinium iodide

A mixture of methyl iodide (1 ml, 15 mmol) and 3-(4-octyloxy-1,2,5-thiadiazol-3-yl) pyridine (3 mmol) in acetone (5 ml) was stirred at room temperature for 18 h. The title compound precipitated from the solution and was collected by filtration to yield 0.81 g (62%).

C. 3-(4-octyloxy-1,2,5-thiadiazol-3-yl)-1,2,5,6-tetrahydro-1-methylpyridine oxalate Sodium borohydride (210 mg, 5.6 mmol) was added to a solution of 3-(4-octyloxy-1,2,5-thiadiazol-3-yl)-1-methylpyridinium iodide (0.81 g, 1.87 mmol) in ethanol (99.9%, 10 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 330 mg. (M.p. 144°–145° C.; M+: 309; Compound 25).

EXAMPLE 23

A. 3-(4-(3-hexynyloxy)-1,2,5-thiadiazol-3-yl)pyridine

To a solution of 3-hexyn-1-ol (880 mg, 9 mmol) and sodium hydride (310 mg, 9 mmol) in dry tetrahydrofuran was added a solution of 3-(4-chloro-1,2,5-thiadiazol-3-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. 3-(4-(3-hexynyloxy)-1,2,5-thiadiazol-3-yl)-1-methylpyridinium iodide

A mixture of methyl iodide (1 ml, 15 mmol) and 3-(4-(3-hexynyloxy)-1,2,5-thiadiazol-3-yl) pyridine (3 mmol) in acetone (5 ml) was stirred at room temperature for 18 h. The title compound precipitated from the solution and was collected by filtration to yield 0.85 g (71%).

C. 3-(4-(3-hexynyloxy)-1,2,5-thiadiazol-3-yl)-1,2,5,6-tetrahydro-1-methylpyridine oxalate

Sodium borohydride (190 mg, 5 mmol) was added to a solution of 3-(4-(3-hexynyloxy)-1,2,5-thiadiazol-3-yl)-1-methylpyridinium iodide (0.85 g, 2.1 mmol) in ethanol (99.9%, 10 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 350 mg. (M.p. 174°–175° C.; M+: 277; Compound 26).

EXAMPLE 24

A. 3-(4-(3-methyl-2-butenyloxy)-1,2,5-thiadiazol-3-yl)pyridine

To a solution of 3-methyl-2-buten-1-ol (780 mg, 9 mmol) and sodium hydride (310 mg, 9 mmol) in dry tetrahydrofuran was added a solution of 3-(4-chloro-1,2,5-thiadiazol-3-yl)pyridine (590 mg, 3 mmol) in dry tetrahydrofuran. The reaction mixture was stirred at room temperature for 0.3 h. Water was added and the mixture was extracted with ether. The ether phase was dried and evaporated to give the title compound.

B. 3-(4-(3-methyl-2-butenyloxy)-1,2,5-thiadiazol-3-yl)-1-methylpyridinium iodide

A mixture of methyl iodide (1 ml, 15 mmol) and 3-(4-(3-methyl-2-butenyloxy)-1, 2,5-thiadiazol-3-yl)pyridine (3 mmol) in acetone (3 ml) was stirred at room temperature for 18 h. The title compound precipitated from the solution and was collected by filtration to yield 0.92 g (79%).

C. 3-(4-(3-methyl-2-butenyloxy)-1,2,5-thiadiazol-3-yl)-1,2,5,6-tetrahydro-1-methylpyridine oxalate

Sodium borohydride (220 mg, 6 mmol) was added to a solution of 3-(4-(3-methyl-2-butenyloxy)-1,2,5-thiadiazol-3-yl)-1-methylpyridinium iodide (0.92 g, 2.3 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 380 mg. (M.p. 150°–151° C.; M+: 265; Compound 27).

EXAMPLE 25

A. 3-(4-(3-butenyl-2-oxy)-1,2,5-thiadiazol-3-yl)pyridine

To a solution of 3-buten-2-ol (650 mg, 9 mmol) and sodium hydride (310 mg, 9 mmol) in dry tetrahydrofuran was added a solution of 3-(4-chloro-1,2,5-thiadiazol-3-yl)pyridine (590 mg, 3 mmol) in dry tetrahydrofuran. The reaction mixture was stirred at room temperature for 18 h. Water was added and the mixture was extracted with ether. The ether phase was dried and evaporated to give the title compound.

B. 3-(4-(3-butenyl-2-oxy)-1,2,5-thiadiazol-3-yl)-1-methylpyridinium iodide

A mixture of methyl iodide (1 ml, 15 mmol) and 3-(4-(3-butenyl-2-oxy)-1,2,5-thiadiazol-3-yl) pyridine (3 mmol) in acetone (3 ml) was stirred at room temperature for 18 h. The title compound precipitated from the solution and was collected by filtration to yield 0.73 g (65%).

C. 3-(4-(3-butenyl-2-oxy)-1,2,5-thiadiazol-3-yl)-1,2,5,6-tetrahydro-1-methylpyridine oxalate

Sodium borohydride (190 mg, 5 mmol) was added to a solution of 3-(4-(3-butenyl-2-oxy)-1,2,5-thiadiazol-3-yl)-1-methylpyridinium iodide (0.73 g, 1.9 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 270 mg. (M.p. 134°–135° C.; M+: 251; Compound 28).

EXAMPLE 26

A. 3-(4-(4-hexenyloxy)-1,2,5-thiadiazol-3-yl)pyridine

To a solution of 4-hexen-1-ol (900 mg, 9 mmol) and sodium hydride (310 mg, 9 mmol) in dry tetrahydrofuran was added a solution of 3-(4-chloro-1,2,5-thiadiazol-3-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. 3-(4-(4-hexenyloxy)-1,2,5-thiadiazol-3-yl)-1-methylpyridinium iodide

A mixture of methyl iodide (1 ml, 15 mmol) and 3-(4-(4-hexenyloxy)-1, 2,5-thiadiazol-3-yl)pyridine (3 mmol) in acetone (5 ml) was stirred at room temperature for 18 h. The title compound precipitated from the solution and was collected by filtration to yield 0.54 g (45%).

C. 3-(4-(4-hexenyloxy)-1,2,5-thiadiazol-3-yl)-1,2,5,6-tetrahydro-1-methylpyridine oxalate Sodium borohydride (150 mg, 4 mmol) was added to a solution of 3-(4-(4-hexenyloxy)-1,2,5-thiadiazol-3-yl)-1-methylpyridinium iodide (0.54 g, 1.3 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 190 mg. (M.p. 151°–152° C.; M+: 279; Compound 29).

EXAMPLE 27

A. trans-3-(4-(3-hexenyloxy)-1,2,5-thiadiazol-3-yl) pyridine

To a solution of trans-3-hexen-1-ol (900 mg, 9 mmol) and sodium hydride (310 mg, 9 mmol) in dry tetrahydrofuran was added a solution of 3-(4-chloro-1,2,5-thiadiazol-3-yl) pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. trans-3-(4-(3-hexenyloxy)-1,2,5-thiadiazol-3-yl)-1-methylpyridinium iodide A mixture of methyl iodide (1 ml, 15 mmol) and trans-3-(4-(3- hexenyloxy)-1, 2,5-thiadiazol-3-yl)pyridine (3 mmol; in acetone (5 ml) was stirred at room temperature for 18 h. The title compound precipitated from the solution and was collected by filtration to yield 0.90 g (75%).

C. trans-3-(4-(3-hexenyloxy)-1,2,5-thiadiazol-3-yl)-1, 2,5,6-tetrahydro-1-methylpyridine oxalate Sodium borohydride (190 mg, 5 mmol) was added to a solution of trans-3-(4-(3-hexenyloxy-1,2,5-thiadiazol-3-yl)-1-methylpyridinium iodide (0.90 g, 2.2 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 420 mg. (M.p. 163°–164° C.; M+: 279; Compound 30).

EXAMPLE 28

A. cis-3-(4-(2-pentenyloxy)-1,2,5-thiadiazol-3-yl)-pyridine

To a solution of cis-2-penten-1-ol (780 mg, 9 mmol) and sodium hydride (310 mg, 9 mmol) in dry tetrahydrofuran was added a solution of 3-(4-chloro-1,2,5-thiadiazol-3-yl) pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. cis-3-(4-(2-pentenyloxy)-1,2,5-thiadiazol-3-yl)-1-methylpyridinium iodide A mixture of methyl iodide (1 ml, 15 mmol) and cis-3-(4-(2-pentenyloxy)-1,2,5-thiadiazol-3-yl) pyridine (3 mmol) in acetone (5 ml) was stirred at room temperature for 18 h. The title compound precipitated from the solution and was collected by filtration to yield 0.53 g (46%).

C. cis-3-(4-(2-pentenyloxy)-1,2,5-thiadiazol-3-yl)-1,2,5,6-tetrahydro-1-methylpyridine oxalate Sodium borohydride (150 mg, 4 mmol) was added to a solution of cis-3-(4-(2-pentenyloxy)-1,2,5-thiadiazol-3-yl)-1-methylpyridinium iodide (0.53 g, 1.3 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 210 mg. (M.p. 143°–144° C.; M+: 265; Compound 31).

EXAMPLE 29

A. cis-3-(4-(2-hexenyloxy)-1,2,5-thiadiazol-3-yl) pyridine

To a solution of cis-2-hexen-1-ol (900 mg, 9 mmol) and sodium hydride (310 mg, 9 mmol) in dry tetrahydrofuran was added a solution of 3-(4-chloro-1,2,5-thiadiazol-3-yl) pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B. cis-3-(4-(2-hexenyloxy)-1,2,5-thiadiazol-3-yl)-1-methylpyridinium iodide

A mixture of methyl iodide (0.5 ml, 7.5 mmol) and cis-3-(4-(2-hexenyloxy)-1, 2,5-thiadiazol-3-yl)pyridine (3 mmol) in acetone (4 ml) was stirred at room temperature for 18 h. The title compound precipitated from the solution and was collected by filtration.

C.
cis-3-(4-(2-hexenyloxy)-1,2,5-thiadiazol-3-yl)-1,2,5,6-tetrahydro-1-methylpyridine oxalate Sodium borohydride (150 mg, 4 mmol) was added to a solution of cis-3-(4-(2-hexenyloxy)-1,2,5-thiadiazol-3-yl)-1-methylpyridinium iodide (0.6 g, 1 mmol) in ethanol (99.9%, 20 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 150 mg. (M.p. 122°–123° C.; M+: 279; Compound 32).

EXAMPLE 30

A. 3-(4-(5-hexenyloxy)-1,2,5-thiadiazol-3-yl)pyridine

To a solution of 5-hexen-1-ol (900 mg, 9 mmol) and sodium hydride (310 mg, 9 mmol) in dry tetrahydrofuran was added a solution of 3-(4-chloro-1,2,5-thiadiazol-3-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B.
3-(4-(5-hexenyloxy)-1,2,5-thiadiazol-3-yl)-1-methylpyridinium iodide

A mixture of methyl iodide (0.5 ml, 7.5 mmol) and 3-(4-(5-hexenyloxy)-1, 2,5-thiadiazol-3-yl)pyridine (3 mmol) in acetone (5 ml) was stirred at room temperature for 18 h. The title compound precipitated from the solution and was collected by filtration to yield 0.75 g (62%).

C.
3-(4-(5-hexenyloxy)-1,2,5-thiadiazol-3-yl)-1,2,5,6-tetrahydro-1-methylpyridine oxalate Sodium borohydride (150 mg, 4 mmol) was added to a solution of 3-(4-(5-hexenyloxy)-1,2,5-thiadiazol-3-yl)-1-methylpyridinium iodide (0.75 g, 1.8 mmol) in ethanol (99.9%, 20 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 250 mg. (M.p. 137°–138° C.; M+: 279; Compound 33).

EXAMPLE 31

A. cis-3-(4-(3-hexenyloxy)-1,2,5-thiadiazol-3-yl)pyridine

To a solution of cis-3-hexen-1-ol (900 mg, 9 mmol) and sodium hydride (310 mg, 9 mmol) in dry tetrahydrofuran was added a solution of 3-(4-chloro-1,2,5-thiadiazol-3-yl) pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B.
cis-3-(4-(3-hexenyloxy)-1,2,5-thiadiazol-3-yl)-1-methylpyridinium iodide

A mixture of methyl iodide (0,5 ml, 7.5 mmol) and cis-3-(4-(3-hexenyloxy)-1, 2,5-thiadiazol-3-yl)pyridine (3 mmol) in acetone (5 ml) was stirred at room temperature for 18 h. The title compound precipitated from the solution and was collected by filtration to yield 0.9 g (46%).

C.
cis-3-(4-(3-hexenyloxy)-1,2,5-thiadiazol-3-yl)-1,2,5,6-tetrahydro-1-methylpyridine oxalate Sodium borohydride (230 mg, 6 mmol) was added to a solution of cis-3-(4-(3-hexenyloxy)-1,2,5-thiadiazol-3-yl)-1-methylpyridinium iodide (0.90 g, 2.2 mmol) in ethanol (99.9%, 15 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 300 mg. (M.p. 149°–150° C.; M+: 279; Compound 34).

EXAMPLE 32

A. trans-3-(4-(2-hexenyloxy)-1,2,5-thiadiazol-3-yl) pyridine

To a solution of trans-2-hexen-1-ol (900 mg, 9 mmol) and sodium hydride (310 mg, 9 mmol) in dry tetrahydrofuran was added a solution of 3-(4-chloro-1,2,5-thiadiazol-3-yl) pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B.
trans-3-(4-(2-hexenyloxy)-1,2,5-thiadiazol-3-yl)-1-methylpyridinium iodide

A mixture of methyl iodide (0.5 ml, 7.5 mmol) and trans-3-(4-(2-hexenyloxy)-1,2,5-thiadiazol-3-yl) pyridine (3 mmol) in acetone (5 ml) was stirred at room temperature for 18 h. The title compound precipitated from the solution and was collected by filtration to yield 1.09 g (90%).

C.
trans-3-(4-(2-hexenyloxy)-1,2,5-thiadiazol-3-yl)-1,2,5,6-tetrahydro-1-methylpyridine oxalate Sodium borohydride (270 mg, 4 mmol) was added to a solution of trans-3-(4-(2-hexenyloxy)-1,2,5-thiadiazol-3-yl)-1-methylpyridinium iodide (1.09 g, 2.7 mmol) in ethanol (99.9%, 20 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 400 mg. (M.p. 130°–131° C.; M+: 279; Compound 35).

EXAMPLE 33

A. 3-(1,2,5-thiadiazol-3-yl)pyridine

To a solution of 1-butanethiol (2.7 g, 30 mmol) and sodium hydride (1.2 g, 30 mmol) in dry tetrahydrofuran was added a solution of 3-(4-chloro-1,2,5-thiadiazol-3-yl)pyridine (1.2 g, 6 mmol) in dry tetrahydrofuran. The reaction mixture was stirred at −10° for 0.5 h. Water was added and the mixture was extracted with ether. The ether phase was dried and evaporated. The residue was purified by column chromatography (SiO$_2$, eluent: ethyl acetate/methylene chloride (1:1)) to give the title compound.

B. 3-(1,2,5-thiadiazol-3-yl)-1-methylpyridinium iodide

A mixture of methyl iodide (1 ml, 15 mmol) and 3-(1,2,5-thiadiazol-3-yl)pyridine (6 mmol) in acetone (5 ml) was stirred at room temperature for 18 h. The title compound precipitated from the solution and was collected by filtration to yield 1.2 g (74%).

C. 3-(1,2,5-thiadiazol-3-yl)-1,2,5,6-tetrahydro-1-methylpyridine oxalate

Sodium borohydride (380 mg, 10 mmol) was added to a solution of 3-(1,2,5-thiadiazol-3-yl)-1-methylpyridinium iodide (1.2 g, 4.4 mmol) in ethanol (99.9%, 20 ml) and the reaction mixture was stirred at −10° C. for 0.5 h. After evaporation the residue was dissolved in water and extracted with ethyl acetate. The dried organic phases were evaporated and the residue purified by column chromatography (SiO$_2$, eluent: ethyl acetate/ methanol (4:1)). The title compound was crystallized as the oxalate salt from acetone to yield 430 mg. (M.p. 189°-190° C.; M+: 181; Compound 36).

EXAMPLE 34

1,2,5,6-tetrahydro-3-(3-hexyloxy-1,2,5-thiadiazol-3-yl)pyridine oxalate

To a solution of 3-(4-hexyloxy-1,2,5-thiadiazol-3-yl)-1,2,5,6-tetrahydro-1-methylpyridine (0.70 g, 2.4 mmol) in 1,2-dichloroethane (20 ml) was added a solution of 1-chloromethyl-chloroformate (0.35 g, 2.4 mmol) in 1,2-dichloroethane at 0° C. The reaction mixture was teated to 40° C. for 2 h and evaporated. The residue was dissolved in methanol and heated to reflux for 1 h and evaporated. The residue was dissolved in diluted sodium hydroxide and extracted with ether. The combined ether phases were dried and evaporated. Crystallization as the oxalate salt from acetone gave the title compound in 72% (620 mg) yield. (M.p. 157°-159° C.; M+: 267; Compound 37).

EXAMPLE 35

A. 3-(4-(2-(2-methoxyethoxy)ethoxy)-1,2,5-thiadiazol-3-yl)pyridine

To a solution of sodium (210 mg, 9 mmol) in 2-(2-methoxyethoxy)ethanol (10 ml) was added 3-(4-chloro-1,2,5-thiadiazol-3-yl) pyridine (590 mg, 3 mmol). The mixture was stirred at 50° C. for 4 h and evaporated. The residue was dissolved in water and extracted with ether. The combined organic phases were dried and evaporated to give the title compound.

B. 3-(4-(2-(2-methoxyethoxy)ethoxy)-1,2,5-thiadiazol-3-yl)-1-methylpyridinium iodide A mixture of methyl iodide (0.5 ml, 9 mmol) and 3-(4-(2-(2-methoxyethoxy)ethoxy)-1, 2,5-thiadiazol-3-yl)pyridine (3 mmol) in acetone (10 ml) was stirred at room temperature for 18 h. The title compound precipitated from the solution and was collected by filtration to yield 0.76 g (60%).

C. 3-(4-(2-(2-methoxyethoxy)ethoxy)-1,2,5-thiadiazol-3-yl)-1, 2,5,6-tetrahydro-1-methylpyridine oxalate Sodium borohydride (150 mg, 4 mmol) was added to a solution of 3-(4-(2-(2-methoxyethoxy)ethoxy)-1,2,5-thiadiazol-3-yl)-1-methylpyridinium iodide (0.76 g, 1.8 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 70 mg. (M.p. 142°-143° C.; M+: 299; Compound 38).

EXAMPLE 36

A. 3-(4-(3-ethoxy-1-propoxy)-1,2,5-thiadiazol-3-yl)pyridine

To a solution of 3-ethoxy-1-propanol (940 mg, 9 mmol) and sodium hydride (310 mg, 9 mmol) in dry tetrahydrofuran was added a solution of 3-(4-chloro-1,2,5-thiadiazol-3-yl)pyridine (590 mg, 3 mmol) in dry tetrahydrofuran. The reaction mixture was stirred at room temperature for 2 h. Water was added and the mixture was extracted with ether. The ether phase was dried and evaporated to give the title compound.

B. 3-(4-(3-ethoxy-1-propoxy)-1,2,5-thiadiazol-3-yl)-1-methylpyridinium iodide A mixture of methyl iodide (0.5 ml, 9 mmol) and 3-(4-ethoxy-1-propoxy-1,2,5-thiadiazol-3-yl) pyridine (3 mmol) in acetone (5 ml) was stirred at room temperature for 18 h. The title compound precipitated from the solution and was collected by filtration.

C. 3-(4-(3-ethoxy-1-propoxy)-1,2,5-thiadiazol-3-yl)-1,2,5,6-tetrahydro-1-methylpyridine oxalate Sodium borohydride (190 mg, 5 mmol) was added to a solution of 3-(4-(3-ethoxy-1-propoxy)-1,2,5-thiadiazol-3-yl)-1-methylpyridinium iodide (3 mmol) in ethanol (99.9%, 15 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 210 mg. (M.p. 149°-150° C.; M+: 283; Compound 39).

EXAMPLE 37

A. 3-(4-(2-ethoxyethoxy)-1,2,5-thiadiazol-3-yl)pyridine

To a solution of 2-ethoxyethanol (1.08 g, 12 mmol) and sodium hydride (410 mg, 12 mmol) in dry tetrahydrofuran was added a solution of 3-(4-chloro-1,2,5-thiadiazol-3-yl) pyridine (790 mg, 4 mmol) in dry tetrahydrofuran. The mixture was stirred at room temperature for 2 h. Water was added and the mixture was extracted with ether. The ether phase was dried and evaporated to give the title compound.

B.
3-(4-(2-ethoxyethoxy)-1,2,5-thiadiazol-3-yl)-1-methylpyridinium iodide

A mixture of methyl iodide (0.5 ml, 9 mmol) and 3-(4-(2-ethoxyethoxy)-1,2,5-thiadiazol-3-yl) pyridine (4 mmol) in acetone (3 ml) was stirred at room temperature for 18 h. The title compound precipitated from the solution and was collected by filtration to yield 1.45 g (92%).

C.
3-(4-(2-ethoxyethoxy)-1,2,5-thiadiazol-3-yl)-1,2,5,6-tetrahydro-1-methylpyridine oxalate Sodium borohydride (350 mg, 9 mmol) was added to a solution of 3-(4-(2-ethoxyethoxy)-1,2,5-thiadiazol-3-yl)-1-methylpyridinium iodide (1.45 g, 3.7 mmol) in ethanol (99.9%, 15 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 640 mg. (M.p. 153°–156° C.; M+: 269; Compound 40).

EXAMPLE 38

A. 3-(4-(2-butoxyethoxy)-1,2,5-thiadiazol-3-yl)pyridine

To a solution of 2-butoxyethanol (1.06 g, 9 mmol) and sodium hydride (310 mg, 9 mmol) in dry tetrahydrofuran was added a solution of 3-(4-chloro-1,2,5-thiadiazol-3-yl)pyridine (590 mg, 3 mmol) in dry tetrahydrofuran. The reaction mixture was stirred at room temperature for 2 h. Water was added and the mixture was extracted with ether. The ether phase was dried and evaporated to give the title compound.

B.
3-(4-(2-butoxyethoxy)-1,2,5-thiadiazol-3-yl)-1-methylpyridinium iodide

A mixture of methyl iodide (0.5 ml, 9 mmol) and 3-(4-(2-butoxyethoxy)-1,2,5-thiadiazol-3-yl) pyridine (3 mmol) in acetone (4 ml) was stirred at room temperature for 18 h. The title compound precipitated from the solution and was collected by filtration to yield 1.07 g (85%).

C.
3-(4-(2-butoxyethoxy)-1,2,5-thiadiazol-3-yl)-1,2,5,6-tetrahydro-1-methylpyridine oxalate Sodium borohydride (230 mg, 6 mmol) was added to a solution of 3-(4-(2-butoxyethoxy)-1,2,5-thiadiazol-3-yl)-1-methylpyridinium iodide (1.07 g, 2.5 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 490 mg. (M.p. 152°–153° C.; M+: 297, Compound 41).

EXAMPLE 39

A.
3-(4-(2-(2-butoxyethoxy)ethoxy)-1,2,5-thiadiazol-3-yl)pyridine

To a solution of 2-(2-butoxyethoxy)ethanol (1.46 g, 9 mmol) and sodium hydride (310 mg, 9 mmol) in dry tetrahydrofuran was added a solution of 3-(4-chloro-1,2,5-thiadiazol-3-yl)pyridine (590 mg, 3 mmol) in dry tetrahydrofuran. The reaction mixture was stirred at room temperature for 1 h. Water was added and the mixture was extracted with ether. The ether phase was dried and evaporated to give the title compound.

B.
3-(4-(2-(2-butoxyethoxy)ethoxy)-1,2,5-thiadiazol-3-yl)-1-methylpyridinium iodide A mixture of methyl iodide (0.5 ml, 9 mmol) and 3-(4-(2-(2-butoxyethoxy) ethoxy)-1,2,5-thiadiazol-3-yl)pyridine (3 mmol) in acetone (5 ml) was stirred at room temperature for 18 h. The title compound precipitated from the solution and was collected by filtration.

C.
3-(4-(2-(2-butoxyethoxy)ethoxy)-1,2,5-thiadiazol-3-yl)-1, 2,5,6-tetrahydro-1-methylpyridine oxalate Sodium borohydride (230 mg, 6 mmol) was added to a solution of 3-(4-(2-(2-butoxyethoxy)ethoxy)-1,2,5-thiadiazol-3-yl)-1-methylpyridinium iodide (3 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 340 mg. (M.p. 90°–91° C.; M+: 341; Compound 42).

EXAMPLE 40

A.
3-(4-(2-(2-ethoxyethoxy)ethoxy)-1,2,5-thiadiazol-3-yl)pyridine

To a solution of 2-(2-ethoxyethoxy)ethanol (1.21 g, 9 mmol) and sodium hydride (310 mg, 9 mmol) in dry tetrahydrofuran was added a solution of 3-(4-chloro-1,2,5-thiadiazol-3-yl) pyridine (590 mg, 3 mmol) in dry tetrahydrofuran. The reaction mixture was stirred at room temperature for 2 h. Water was added and the mixture was extracted with ether. The ether phase was dried and evaporated to give the title compound.

B.
3-(4-(2-(2-ethoxyethoxy)ethoxy)-1,2,5-thiadiazol-3-yl)-1-methylpyridinium iodide A mixture of methyl iodide (0.5 ml, 9 mmol) and 3-(4-(2-(2-ethoxyethoxy)ethoxy)-1, 2,5-thiadiazol-3-yl)pyridine (3 mmol) in acetone (5 ml) was stirred at room temperature for 18 h. The title compound precipitated from the solution and was collected by filtration.

C.
3-(4-(2-(2-ethoxyethoxy)ethoxy)-1,2,5-thiadiazol-3-yl)-1,2,5,6-tetrahydro-1-methylpyridine oxalate Sodium borohydride (230 mg, 6 mmol) was added to a solution of 3-(4-(2-(2-ethoxyethoxy)ethoxy)-1,2,5-thiadiazol-3-yl)-1-methylpyridinium iodide (3 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 290 mg. (M.p. 115°–116° C.; M+: 313; Compound 43).

EXAMPLE 41

A. 3-(4-(4-methylpiperidino)-1,2,5-thiadiazol-3-yl)pyridine

A solution of 3-(4-chloro-1,2,5-thiadiazol-3-yl)pyridine (10.80 g, 4 mmol) and 4-methylpiperidine (1.96 g, 20 mmol) in DMF (10 ml) was heated at 100° C. for 3 h. After evaporation water was added to the residue and extracted with ether. The combined and dried organic phases were evaporated and the residue purified by column chromatography (SiO$_2$, eluent: ethyl acetate/methylene chloride (1:2)). Yield: 0.8 g (77%).

B.
3-(4-(4-methylpiperidino)-1,2,5-thiadiazol-3-yl)-1-methylpyridinium iodide

A mixture of methyl iodide (0.5 ml, 8 mmol) and 3-(4-(4-methylpiperidino)-1, 2,5-thiadiazol-3-yl)pyridine (0.8 g, 3.1 mmol) in acetone (5 ml) was stirred at room temperature for 18 h. The title compound precipitated from the solution and was collected by filtration to yield 1.14 g (92%).

C. 3-(4-(4-methylpiperidino)-1,2,5-thiadiazol-3-yl)-1,2,5,6-tetrahydro-1-methylpyridine oxalate Sodium borohydride (270 mg, 7 mmol) was added to a solution of 3-(4-(4-methylpiperidino)-1,2,5-thiadiazol-3-yl)-1-methylpyridinium iodide (1.14 g, 2.8 mmol) in ethanol (99.9%, 20 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 450 mg. (M.p. 106°–107° C.; M+: 278; Compound 44).

EXAMPLE 42

A. 3-(4-morpholino-1,2,5-thiadiazol-3-yl)pyridine

A solution of 3-(4-chloro-1,2,5-thiadiazol-3-yl)pyridine (0.59 g, 3 mmol) and morpholine (1.3 g, 15 mmol) in DMF (5 ml) was heated at 100° C. for 3 h. After evaporation water was added to the residue and extracted with ether. The combined and dried organic phases were evaporated and the residue purified by column chromatography (SiO$_2$, eluent: ethyl acetate/methylene chloride (1:1)). Yield: 0.68 g (91%).

B.
3-(4-morpholino-1,2,5-thiadiazol-3-yl)-1-methylpyridinium iodide

A mixture of methyl iodide (0.5 ml, 8 mmol) and 3-(4-morpholino-1, 2,5-thiadiazol-3-yl)pyridine (680 mg, 2.7 mmol) in acetone (5 ml) was stirred at room temperature for 18 h. The title compound precipitated from the solution and was collected by filtration to yield 1.0 g (94%).

C.
3-(4-morpholino-1,2,5-thiadiazol-3-yl)-1,2,5,6-tetrahydro-1-methylpyridine oxalate Sodium borohydride (380 mg, 10 mmol) was added to a solution of 3-(4-morpholino-1,2,5-thiadiazol-3-yl)-1-methylpyridinium iodide (1.53 g, 3g mmol) in ethanol (99.9%, 30 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 470 mg. (M.p. 177°–178° C.; M+: 266; Compound 45).

EXAMPLE 43

A. 3-(4-hexylamino-1,2,5-thiadiazol-3-yl)pyridine

A solution of 3-(4-chloro-1,2,5-thiadiazol-3-yl)pyridine (0.59 g, 3 mmol) and hexylamine (1.52 g, 15 mmol) in DMSO (5 ml) was heated at 100° C. for 48 h. After evaporation, water was added to the residue and extracted with ether. The combined organic extracts were dried and evaporated to give the title compound.

B.
3-(4-hexylamino-1,2,5-thiadiazol-3-yl)-1-methylpyridinium iodide

A mixture of methyl iodide (0.6 ml, 9.6 mmol) and 3-(4-hexylamino-1,2,5-thiadiazol-3-yl) pyridine (3.2 mmol) in acetone (5 ml) was stirred at room temperature for 18 h and evaporated.

C.
3-(4-hexylamino-1,2,5-thiadiazol-3-yl)-1,2,5,6-tetrahydro-1-methylpyridine oxalate Sodium borohydride (380 mg, 10 mmol) was added to a solution of 3-(4-hexylamino-1,2,5-thiadiazol-3-yl)-1-methylpyridinium iodide (4.2 mmol) in ethanol (99.9%, 25 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 490 mg. (M.p. 102°–103° C.; M+: 280; Compound 46).

EXAMPLE 44

A. 3-(4-propylthio-1,2,5-thiadiazol-3-yl)pyridine

Sodium hydrogen sulfide (220 mg, 3 mmol) was added over 30 min. to a solution of 3-(4-chloro-1,2,5-thiadiazol-3-yl)pyridine (0.59 g, 3 mmol) in DMF (20 ml) at room temperature. Potassium carbonate (1.24 g, 9 mmol) and iodopropan (0.76 g, 4.5 mmol) were added. The reaction mixture was stirred at room temperature for 30 min. Water was added and the mixture extracted with ether. The combined ether phases were dried and evaporated to give the title compound in 89% (0.63 g) yield.

B. 3-(4-propylthio-1,2,5-thiadiazol-3-yl)-1-methyl-pyridinium iodide

A mixture of methyl iodide (0.5 ml, 8 mmol) and 3-(4-propylthio-1,2,5-thiadiazol-3-yl) pyridine (0.63 g, 2.6 mmol) in acetone (5 ml) was stirred at room temperature for 18 h and evaporated.

C. 3-(4-propylthio-1,2,5-thiadiazol-3-yl)-1,2,5,6-tetrahydro-1-methylpyridine oxalate Sodium borohydride (200 mg, 5 mmol) was added to a solution of 3-(4-propylthio-1,2,5-thiadiazol-3-yl)-1-methylpyridinium iodide (2.6 mmol) in ethanol (99.9%, 15 ml) and the reaction mixture was stirred at −10° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 310 mg. (M.p. 138°–139° C.; M+: 255; Compound 47).

EXAMPLE 45

A. 3-(4-butylthio-1,2,5-thiadiazol-3-yl)pyridine

Sodium hydrogen sulfide (0.5 g, 6.8 mmol) was added to a solution of 3-(4-chloro-1,2,5-thiadiazol-3-yl)pyridine (0.5 g, 2.5 mmol) in DMF (20 ml) at room temperature and the reaction mixture was stirred for 30 min. Potassium carbonate (2 g, 14.5 mmol) and butyliodide (1 ml, 8.8 mmol) were added and the reaction mixture was stirred for additionally 10 min. Water (50 ml) was added and extracted with ether. The combined ether phases were dried and evaporated to give the title compound. Yield: 0.6 g.

B. 3-(4-butylthio-1,2,5-thiadiazol-3-yl)-1-methyl-pyridinium iodide

Methyl iodide (1 ml, 15 mmol) was added to a solution of 3-(4-butylthio-1,2,5-thiadiazol-3-yl)pyridine (0.6 g, 2.3 mmol) and the reaction mixture was stirred at room temperature for 48 h and evaporated.

C. 3-(4-butylthio-1,2,5-thiadiazol-3-yl)-1,2,5,6-tetrahydro-1-methylpyridine oxalate Sodium borohydride (250 mg, 6.2 mmol) was added to a solution of 3-(4-butylthio-1,2,5-thiadiazol-3-yl)-1-methylpyridinium iodide (2.3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 300 mg. (M.p. 148°–150° C.; M+: 269; Compound 48).

EXAMPLE 46

A. 3-(4-methylthio-1,2,5-thiadiazol-3-yl)pyridine

Sodium hydrogen sulfide (0.5 g, 6.8 mmol) was added to a solution of 3-(4-chloro-1,2,5-thiadiazol-3-yl)pyridine (0.5 g, 2.5 mmol) in DMF (20 ml) at room temperature and the reaction mixture was stirred for 30 min. Potassium carbonate (2 g, 14.5 mmol) and methyliodide (1 ml, 15 mmol) were added and the reaction mixture was stirred for additionally 10 min. Water (50 ml) was added and extracted with ether. The combined ether phases were dried and evaporated to give the title compound. Yield: 0.5 g.

B. 3-(4-methylthio-1,2,5-thiadiazol-3-yl)-1-methyl-pyridinium iodide

Methyl iodide (1 ml, 15 mmol) was added to a solution of 3-(4-methylthio-1,2,5-thiadiazol-3-yl)pyridine (0.5 g, 2.3 mmol) and the reaction mixture was stirred at room temperature for 48 h and evaporated.

C. 3-(4-methylthio-1,2,5-thiadiazol-3-yl)-1,2,5,6-tetrahydro-1-methylpyridine oxalate Sodium borohydride (250 mg, 6.2 mmol) was added to a solution of 3-(4-methylthio-1,2,5-thiadiazol-3-yl)-1-methylpyridinium iodide (2.3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 300 mg. (M.p. 169°–170° C.; M+: 227; Compound 49).

EXAMPLE 47

A. alpha-oximino-3-pyridylacetonitrile 3-pyridylacetonitrile (47.2 g, 400 mmol) was dissolved in a solution of sodium hydroxide (16 g, 400 mmol) in methanol (100 ml). Methylnitrite, generated by dropping a solution of concentrated sulphuric acid (12.8 ml) and water (26 ml) to a solution of sodium nitrite (33.2 g, 480 mmol) in water (20 ml) and methanol (20 ml), was bobled through the 3-pyridylacetonitrile solution at 0° C. The reaction mixture was stirred at 0° C. for 1 h and the precipitate collected by filtration. The precipitate was washed with a little methanol to give the wanted product in 70% (41.1 g) yield. M+: 147.

B. alpha-oximino-3-pyridylacetamidoxime

A mixture of alpha-oximino-3-pyridylacetonitrile (41.0 g, 279 mmol), hydroxylamine hydrochloride (21.5 g, 310 mmol) and sodium acetate (50.8 g, 620 mmol) in ethanol (99.9%, 500 ml) was refluxed for 4 h. After cooling, the precipitate was collected by filtration and dried. The precipitate contained the wanted product and sodium acetate (85 g, 168%); M+: 180.

C. 3-(4-amino-1,2,5-oxadiaxol-3-yl)pyridine

Crude alpha-oximino-3-pyridylacetamidoxime (5 g) and phosphorus pentachloride (5 g) was refluxed in dry ether (250 ml) for 6 h. Water and potassium carbonate to alkaline pH was added and the phases separated. The aqueous phase was extracted with ether and the combined ether phases dried. Evaporation of the ether phases gave the title compound in 850 mg yield; M+: 162.

D.
3-(4-amino-1,2,5-oxadiazol-3-yl)-1-methylpyridinium iodide

To a solution of 3-(4-amino-1,2,5-oxadiazol-3-yl)pyridine (870 mg, 5.3 mmol) in acetone (20 ml) was added methyl iodide (990 μl, 16 mmol) and the reaction mixture was stirred overnight at room temperature. The title compound precipitated and was collected by filtration (1.1 g, 69%).

E.
3-(4-amino-1,2,5-oxadiazol-3-yl)-1,2,5,6-tetrahydro-1-methylpyridine oxalate Sodium borohydride (262 mg, 6.9 mmol) was added to a solution of 3-(4-amino-1,2,5-oxadiazol-3-yl)-1-methylpyridinium iodide (1.05 g, 3.45 mmol) in methanol (80 ml) at 0° C. After 15 min. water (40 ml) was added and the mixture extracted with ether. The ether phase was dried, evaporated and purified by column chromatography (eluent: ethyl acetate:methanol (2:1)). Crystallization from acetone with oxalic acid gave the title compound in 310 mg (50%) yield. (M.p. 181°–183° C.; M+: 180; Compound 50).

EXAMPLE 48

A. 3-(4-acetylamino-1,2,5-oxadiazol-3-yl)pyridine

Crude hydroxyimino-3-pyridylmethylamidoxime (4.5 g) and polyphosphoric acid (49 g) was stirred at 100° C. for 18 h. After cooling to room temperature aqueous ammonia (25%) was added slowly to pH>9 and the precipitate collected by filtration. The precipitate was dissolved in water and extracted with methylene chloride. The organic phases were dried and evaporated to give the title compound in 430 mg yield.

B.
3-(4-acetylamino-1,2,5-oxadiazol-3-yl)-1-methylpyridinium iodide

Methyl iodide (450 μl, 7.2 mmol) was added to a solution of 3-(4-acetylamino-1,2,5-oxadiazol-3-yl)pyridine (490 mg, 2.4 mmol) in acetone. The reaction mixture was stirred at room temperature for 18 h and the precipitate collected by filtration. Yield: 640 mg (77%).

C.
3-(4-acetylamino-1,2,5-oxadiazol-3-yl)-1,2,5,6-tetrahydro-1-methylpyridine oxalate Sodium borohydride (140 mg, 3.7 mmol) was added to a solution of 3-(4-acetylamino-1,2,5-oxadiazol-3-yl)-1-methylpyridinium iodide (640 mg, 1.85 mmol) in methanol (15 ml) at 0° C. After 15 min. water (10 ml) was added and the reaction mixture extracted with ether. The combined ether phases were dried and evaporated. Crystallization from acetone with oxalic acid gave the title compound in 140 mg yield. (M.p. 180°–184° C.; M+: 222; Compound 51).

EXAMPLE 49

A. 3-(1,2,5-oxadiazol-3-yl)pyridine and 3-(4-chloro-1,2,5-oxadiazol-3-yl)pyridine To a solution of 3-(4-amino-1,2,5-oxadiazol-3-yl)pyridine (1.0 g, 6.2 mmol) in glacial acetic acid (16 ml) and concentrated hydrochloric acid (5.2 ml) was added $CuCl_2$ (938 mg, 7 mmol) and cupper coils (100 mg) at 0° C. After 10 min. a solution of sodium nitrite (483 mg, 7 mmol) in water (3 ml) was added dropwise at 5° C. The reaction mixture was stirred additionally 30 min. at 0° C. Aqueous sodium hydroxide (2N) was added to alkaline pH and the mixture extracted with ether. The ether phases were dried and evaporated to give a mixture of the title compounds. Separation by column chromatography ($SiO_2$, eluent: ethyl acetate) gave the chloro compound, upper spot, in 230 mg yield, and the unsubstituted product, lower spot, in 60 mg yield.

B.
3-(4-chloro-1,2,5-oxadiazol-3--yl)-1-methylpyridinium iodide

Methyl iodide (1 ml, 15 mmol) was added to a solution of 3-(4-chloro-1,2,5-oxadiazol-3-yl)pyridine (230 mg, 1.2 mmol) in acetone. The reaction mixture was stirred at room temperature for 18 h and evaporated to give the title compound.

C.
3-(4-chloro-1,2,5-oxadiazol-3-yl)-1,2,5,6-tetrahydro-1-methylpyridine oxalate Sodium borohydride (119 mg, 3.2 mmol) was added to a solution of 3-(4-chloro-1,2,5-oxadiazol-3-yl)-1-methylpyridinium iodide (1.2 mmol) in methanol (5 ml) at 0° C. After 15 min. water was added and the mixture extracted with ether. The ether phases were dried and evaporated. Crystallization from acetone with oxalic acid and recrystallization from acetone gave the title compound in 60 mg yield. (M.p. 126°–129° C.; M+: 198 and 200; Compound 52).

EXAMPLE 50

A. 3-(1,2,5-oxadiazol-3-yl)-1-methylpyridinium iodide

Methyl iodide (1 ml, 15 mmol) was added to a solution of 3-(1,2,5-oxadiazol-3-yl)pyridine (430 mg, 2.9 mmol) in acetone (20 ml). The reaction mixture was stirred at room temperature for 18 h. The product precipitated from the solution and the title compound was collected by filtration in 82% (700 mg) yield.

B.
3-(1,2,5-oxadiazol-3-yl)-1,2,5,6-tetrahydro-1-methylpyridine oxalate

Sodium borohydride (168 mg, 4.4 mmol) was added to a solution of 3-(1,2,5-oxadiazol-3-yl)-1-methylpyridinium iodide (640 mg, 2.2 mmol) in methanol (15 ml) and water (2 ml) at 0° C. After 15 min. water was added and the mixture extracted with ether. The combined ether phases were dried and evaporated. The residue was crystallized as the oxalate salt from acetone giving the title compound in 100 mg yield. (M.p. 238°–240° C. dec.; M+: 165; Compound 53).

EXAMPLE 51

A. 3-(4-hexyloxy-1,2,5-oxadiazol-3-yl)pyridine

To a solution of sodium (100 mg, 4.3 mmol) in 1-hexanol (10 ml) was added 3-(4-chloro-1,2,5-oxadiazol-3-yl)pyridine (180 mg, 1 mmol). The mixture was stirred at 25° C. for 18 h and evaporated. The residue was dissolved in water and extracted with ether. The combined organic phases were dried and evaporated to give the title compound.

B.
3-(4-hexyloxy-1,2,5-oxadiazol-3-yl)-1-methyl-
pyridinium iodide

A mixture of methyl iodide (1 ml, 15 mmol) and 3-(4-hexyloxy-1, 2,5-oxadiazol-3-yl)pyridine (1 mmol) in acetone (5 ml) was stirred at room temperature for 18 h and evaporated to give the title compound.

C.
3-(4-hexyloxy-1,2,5-oxadiazol-3-yl)-1,2,5,6-tetrahydro-1-methylpyridine oxalate Sodium borohydride (76 mg, 2 mmol) was added to a solution of 3-(4-hexyloxy-1,2,5-oxadiazol-3-yl)-1-methylpyridinium iodide (1 mmol) in methanol (5 ml) and the reaction mixture was stirred at 0° C. for 15 min. After evaporation the residue was dissolved in water and extracted with ether. The dried organic phases were evaporated and the residue purified by column chromatography (SiO$_2$, eluent: ethyl acetate/methanol (4:1)). The title compound was crystallized as the oxalate salt from acetone to yield 60 mg. (M.p. 143°–147° C.; M+: 265; Compound 54).

EXAMPLE 52

A. 3-(4-butyloxy-1,2,5-oxadiazol-3-yl)pyridine

To a solution of sodium (150 mg, 6.5 mmol) in 1-butanol (5 ml) was added 3-(4-chloro-1,2,5-oxadiazol-3-yl)pyridine (350 mg, 1.9 mmol). The mixture was stirred at 25° C. for 2 h and evaporated. The residue was dissolved in water and extracted with ether. The combined organic phases were dried and evaporated to give the title compound.

B.
3-(4-butyloxy-1,2,5-oxadiazol-3-yl)-1-methylpyridinium iodide

A mixture of methyl iodide (1 ml, 15 mmol) and 3-(4-butyloxy-1,2,5- oxadiazol-3-yl) pyridine (1.9 mmol) in acetone (10 ml) was stirred at room temperature for 18 h and evaporated.

C.
3-(4-butyloxy-1,2,5-oxadiazol-3-yl)-1,2,5,6-tetrahydro-1-methylpyridine oxalate Sodium borohydride (148 mg, 3.8 mmol) was added to a solution of 3-(4-butyloxy-1,2,5-oxadiazol-3-yl)-1-methylpyridinium iodide (1.9 mmol) in methanol (20 ml) and the reaction mixture was stirred at 0° C. for 15 min. After evaporation the residue was dissolved in water and extracted with ether. The dried organic phases were evaporated and the residue purified by column chromatography (SiO$_2$, eluent: ethyl acetate/methanol (4:1)). The title compound was crystallized as the oxalate salt from acetone to yield 120 mg. (M.p. 132°–135° C.; M+: 237; Compound 55).

EXAMPLE 53

A. 3-(4-(3-hexynyloxy)-1,2,5-oxadiazol-3-yl)pyridine

To a solution of 3-hexyn-1-ol (g80 mg, 10 mmol) and sodium hydride (240 mg, 10 mmol) in dry tetrahydrofuran was added a solution of 3-(4-chloro-1,2,5-oxadiazol-3-yl)pyridine (450 mg, 2.5 mmol) in dry tetrahydrofuran. The reaction mixture was stirred at room temperature for 2 h. Water was added and the mixture was extracted with ether. The ether phase was dried and evaporated to give the title compound.

B.
3-(4-(3-hexynyloxy)-1,2,5-oxadiazol-3-yl)-1-methyl-
pyridinium iodide

A mixture of methyl iodide (1.5 ml, 22 mmol) and 3-(4-(3-hexynyloxy)-1, 2,5-oxadiazol-3-yl)pyridine (2.5 mmol) in acetone (20 ml) was stirred at room temperature for 18 h and evaporated to give the title compound.

C.
3-(4-(3-hexynyloxy)-1,2,5-oxadiazol-3-yl)-1,2,5,6-tetrahydro-1-methylpyridine oxalate Sodium borohydride (190 mg, 5 mmol) was added to a solution of 3-(4-(3-hexynyloxy)-1,2,5-oxadiazol-3-yl)-1-methylpyridinium iodide (2.5 mmol) in methanol (20 ml) and the reaction mixture was stirred at 0° C. for 15 min. After evaporation the residue was dissolved in water and extracted with ether. The dried organic phases were evaporated and the residue purified by column chromatography (SiO$_2$, eluent: ethyl acetate/methanol (4:1)). The title compound was crystallized as the oxalate salt from acetone to yield 50 mg. (M.p. 159°–161° C.; M+: 261; Compound 56).

EXAMPLE 54

3-(4-pentyl-1,2,5-thiadiazol-3-yl)-1,2,5,6-tetrahydro-1-methylpyridinium oxalate To a solution of 3-(4-chloro-1,2,5-thiadiazol-3-yl)-1,2,5,6-tetrahydro-1-methylpyridine (450 mg, 1.5 mmol) in tetrahydrofuran (20 ml) was added slowly a solution of pentylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was crystallized as the oxalate salt from acetone in 300 mg (58%) yield. Recrystallization from ethanol gave the title compound in 125 mg (24%) yield. (M.p. 156°–157° C.; M+: 251; Compound 57).

EXAMPLE 55

3-(4-heptyl-1,2,5-thiadiazol-3-yl)-1,2,5,6-tetrahydro-1-methylpyridinium oxalate To a solution of 3-(4-chloro-1,2,5-thiadiazol-3-yl)-1,2,5,6-tetrahydro-1-methylpyridine (450 mg, 1.5 mmol) in tetrahydrofuran (20 ml) was added slowly a solution of heptylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was crystallized as the oxalate salt from acetone in 400 mg (73%) yield. (M.p. 151°–152° C.; M+: 274; Compound 58).

EXAMPLE 56

3-(4-(5-hexenyl)-1,2,5-thiadiazol-3-yl)-1,2,5,6-tetrahydro-1-methylpyridinium oxalate To a solution of 3-(4-chloro-1,2,5-thiadiazol-3-yl)-1,2,5,6-tetrahydro-1-methylpyridine (450 mg, 1.5 mmol) in tetrahydrofuran (20 ml) was added slowly a solution of 5-hexenylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was purified by column chromatography (SiO$_2$, eluent: ethyl acetate/methanol (4:1)). The title compound was crystallized as the oxalate salt from acetone in 340 mg (64%) yield. (M.p. 113°–115° C.; M+: 263; Compound 59).

EXAMPLE 57

3-(4-octyl-1,2,5-thiadiazol-3-yl)-1,2,5,6-tetrahydro-1-methylpyridinium oxalate

To a solution of 3-(4-chloro-1,2,5-thiadiazol-3-yl)-1,2,5,6-tetrahydro-1-methylpyridine (450 mg, 1.5 mmol) in tetrahydrofuran (20 ml) was added slowly a solution of octylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was purified by column chromatography (SiO$_2$, eluent: ethyl acetate/methanol (4:1)). The title compound was crystallized as the oxalate salt from acetone in 430 mg (75%) yield. (M.p. 157°–158° C.; M+: 293; Compound 60).

EXAMPLE 58

3-(4-isobutyl-1,2,5-thiadiazol-3-yl)-1,2,5,6-tetrahydro-1-methylpyridinium oxalate To a solution of 3-(4-chloro-1,2,5-thiadiazol-3-yl)-1,2,5,6-tetrahydro-1-methylpyridine (300 mg, 1.5 mmol) in tetrahydrofuran (20 ml) was added slowly a solution of isobutylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was purified by column chromatography (SiO$_2$, eluent: ethyl acetate/methanol (4:1)). The title compound was crystallized as the oxalate salt from acetone in 350 mg (76%) yield. (M.p. 148°–149° C.; M+: 237; Compound 61).

EXAMPLE 59

3-(4-cyclopropylmethyl-1,2,5-thiadiazol-3-yl)-1,2,5,6-tetrahydro-1-methylpyridinium oxalate To a solution of 3-(4-chloro-1,2,5-thiadiazol-3-yl)-1,2,5,6-tetrahydro-1-methylpyridine (300 mg, 1.4 mmol) in tetrahydrofuran (20 ml) was added slowly a solution of cyclopropylmethylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was purified by column chromatography (SiO$_2$, eluent: ethyl acetate/methanol (4:1)). The title compound was crystallized as the oxalate salt from acetone in 380 mg (83%) yield. (M.p. 147°–148° C.; M+: 235; Compound 62).

EXAMPLE 60

3-(4-propyl-1,2,5-thiadiazol-3-yl)-1,2,5,6-tetrahydro-1-methylpyridinium oxalate To a solution of 3-(4-chloro-1,2,5-thiadiazol-3-yl)-1,2,5,6-tetrahydro-1-methylpyridine (450 mg, 1.5 mmol) in tetrahydrofuran (20 ml) was added slowly a solution of propylmagnesium bromide (1.5 mmol) in tetrahydrofuran at 0° C. The reaction mixture was stirred for 10 min. and water (20 ml) was added. The product was extracted with ether (3×100 ml) and the dried ether phases evaporated. The residue was crystallized as the oxalate salt from acetone in 350 mg (75%) yield. (M.p. 141°–142° C.; M+: 223; Compound 63).

EXAMPLE 61

A. 3-(4-octylthio-1,2,5-thiadiazol-3-yl)pyridine

Sodium hydrogen sulfide (0.25 g, 3.3 mmol) was added to a solution of 3-(4-chloro-1,2,5-thiadiazol-3-yl)pyridine (0.59 g, 3 mmol) in DMF (20 ml) at room temperature and the reaction mixture was stirred for 30 min. Potassium carbonate (1.24 g, 9 mmol) and 1-bromooctane (0.80 ml, 4.5 mmol) were added and the reaction mixture was stirred for additionally 10 min. Water (50 ml) was added and extracted with ether. The combined ether phases were dried and evaporated to give the title compound.

B. 3-(4-octylthio-1,2,5-thiadiazol-3-yl)-1-methylpyridinium iodide

Methyl iodide (0.5 ml, 7.5 mmol) was added to a solution of 3-(4-octylthio-1,2,5-thiadiazol-3-yl)pyridine (3 mmol) and the reaction mixture was stirred at room temperature for 48 h and evaporated.

C. 3-(4-octylthio-1,2,5-thiadiazol-3-yl)-1,2,5,6-tetrahydro-1-methylpyridine oxalate Sodium borohydride (270 mg, 7 mmol) was added to a solution of 3-(4-octylthio-1,2,5-thiadiazol-3-yl)-1-methylpyridinium iodide (3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 400 mg. (M.p. 121°–122° C.; M+: 325; Compound 64).

EXAMPLE 62

A. 3-(4-ethylthio-1,2,5-thiadiazol-3-yl)pyridine

Sodium hydrogen sulfide (0.25 g, 3.3 mmol) was added to a solution of 3-(4-chloro-1,2,5-thiadiazol-3-yl)pyridine (0.59 g, 3 mmol) in DMF (20 ml) at room temperature and the reaction mixture was stirred for 30 min. Potassium carbonate (1.24 g, 9 mmol) and ethyl iodide (0.36 ml, 4.5 mmol) were added and the reaction mixture was stirred for additionally 10 min. Water (50 ml) was added and extracted with ether. The combined ether phases were dried and evaporated to give the title compound.

B. 3-(4-ethylthio-1,2,5-thiadiazol-3-yl)-1-methylpyridinium iodide

Methyl iodide (0.5 ml, 7.5 mmol) was added to a solution of 3-(4-ethylthio-1,2,5-thiadiazol-3-yl)pyridine (3 mmol) and the reaction mixture was stirred at room temperature for 48 h and evaporated.

C. 3-(4-ethylthio-1,2,5-thiadiazol-3-yl)-1,2,5,6-tetrahydro-1-methylpyridine oxalate Sodium borohydride (270 mg, 7 mmol) was added to a solution of 3-(4-ethylthio-1,2,5-thiadiazol-3-yl)-1-methylpyridinium iodide (3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 490 mg. (M.p. 145°–146° C.; M$^+$: 241; Compound 65).

EXAMPLE 63

A. 3-(4-pentylthio-1,2,5-thiadiazol-3-yl)pyridine

Sodium hydrogen sulfide (0.25 g, 3.3 mmol) was added to a solution of 3-(4-chloro-1,2,5-thiadiazol-3-yl)pyridine (0.59 g, 3 mmol) in DMF (20 ml) at room temperature and the reaction mixture was stirred for 30 min. Potassium carbonate (1.24 g, 9 mmol) and pentyl bromide (700 mg, 4.5 mmol) were added and the reaction mixture was stirred for additionally 10 min. Water (50 ml) was added and extracted with ether. The combined ether phases were dried and evaporated to give the title compound.

B. 3-(4-pentylthio-1,2,5-thiadiazol-3-yl)-1-methylpyridinium iodide

Methyl iodide (0.5 ml, 7.5 mmol) was added to a solution of 3-(4-pentylthio-1,2,5-thiadiazol-3-yl)pyridine (3 mmol) and the reaction mixture was stirred at room temperature for 48 h and evaporated.

C. 3-(4-pentylthio-1,2,5-thiadiazol-3-yl)-1,2,5,6-tetrahydro-1-methylpyridine oxalate Sodium borohydride (300 mg, 8 mmol) was added to a solution of 3-(4-pentylthio-1,2,5-thiadiazol-3-yl)-1-methylpyridinium iodide (3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 430 mg. (M.p. 136°–138° C.; M$^+$: 283; Compound 66).

EXAMPLE 64

A. 3-(4-hexylthio-1,2,5-thiadiazol-3-yl)pyridine

Sodium hydrogen sulfide (0.25 g, 3.3 mmol) was added to a solution of 3-(4-chloro-1,2,5-thiadiazol-3-yl)pyridine (0.59 g, 3 mmol) in DMF (20 ml) at room temperature and the reaction mixture was stirred for 30 min. Potassium carbonate (1.24 g, 9 mmol) and hexyl bromide (0.63 ml, 4.5 mmol) were added and the reaction mixture was stirred for additionally 10 min. Water (50 ml) was added and extracted with ether. The combined ether phases were dried and evaporated to give the title compound.

B. 3-(4-hexylthio-1,2,5-thiadiazol-3-yl)-1-methylpyridinium iodide

Methyl iodide (1 ml, 15 mmol) was added to a solution of 3-(4-hexylthio-1,2,5-thiadiazol-3-yl)pyridine (3 mmol) and the reaction mixture was stirred at room temperature for 48 h and evaporated.

C. 3-(4-hexylthio-1,2,5-thiadiazol-3-yl)-1,2,5,6-tetrahydro-1-methylpyridine oxalate Sodium borohydride (230 mg, 6 mmol) was added to a solution of 3-(4-hexylthio-1,2,5-thiadiazol-3-yl)-1-methylpyridinium iodide (3 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 350 mg. (M.p. 126°–127° C.; M$^+$: 297; Compound 67).

It is to be understood that the invention is not to be limited to the exact details of operation, or to the exact compounds, compositions, methods, procedures, or embodiments shown and described, as obvious modifications and equivalents will be apparent to one skilled in the art, and the invention is therefore to be limited only by the full scope of the appended claims.

We claim:

1. A compound of formula I

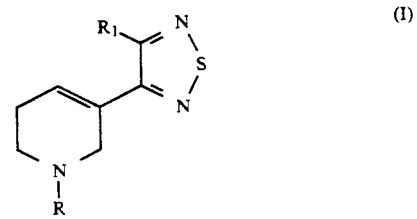

wherein
R is H or CH$_3$; and
R$^1$ is —OR$^2$ wherein R$^2$ is C$_{5-6}$-alkenyl or C$_{5-6}$-alkynyl; or a pharmaceutically acceptable salt thereof.

2. The compound according to claim 1 which is cis-3-(4-(2-pentenyloxy)-1,2,5-thiadiazol-3-yl)-1,2,5,6-tetrahydro-1-methylpyridine or a pharmaceutically acceptable salt thereof.

3. The compound according to claim 1 which is 3-(4-(5-hexenyloxy)-1,2,5-thiadiazol-3-yl)-1,2,5,6-tetrahydro-1-methylpyridine or a pharmaceutically acceptable salt thereof.

4. The compound according to claim 1 which is 3-(4-(3-hexynyloxy)-1,2,5-thiadiazol-3-yl)-1,2,5,6-tetrahydro-1-methylpyridine or a pharmaceutically acceptable salt thereof.

5. The compound according to claim 1 which is cis-3-(4-(3-hexenyloxy)-1,2,5-thiadiazol-3-yl)-1,2,5,6-tetrahydro-1-methylpyridine or a pharmaceutically acceptable salt thereof.

6. The compound according to claim 1 which is trans-3-(4-(3-hexenyloxy)-1,2,5-thiadiazol-3-yl)-1,2,5,6-tetrahydro-1-methylpyridine or a pharmaceutically acceptable salt thereof.

7. A compound of formula I

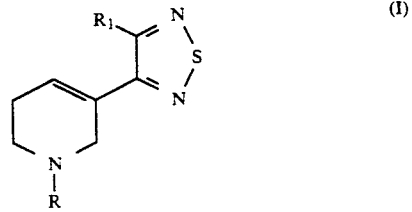

wherein
R is H or CH$_3$; and $R^1$ is —$SR^3$ wherein $R^3$ is $C_{4-6}$-alkenyl or $C_{4-6}$-alkynyl; or a pharmaceutically acceptable salt thereof.

8. A compound of formula I

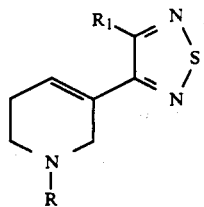

(I)

wherein

R is H; and $R^1$ is —$SR^4$ wherein $R^4$ is $C_{4-6}$-alkyl; or a pharmaceutically acceptable salt thereof.

9. A pharmaceutical composition suitable for use in stimulating the cognitive functions of the forebrain and hippocampus of mammals, including humans, comprising an effective amount of a compound according to claim 1 together with a pharmaceutically acceptable carrier or diluent.

10. A pharmaceutical composition suitable for use in stimulating the cognitive functions of the forebrain and hippocampus of mammals, including humans, comprising an effective amount of a compound according to claim 7 together with a pharmaceutically acceptable carrier or diluent.

11. A pharmaceutical composition suitable for use in stimulating the cognitive functions of the forebrain and hippocampus of mammals, including humans, comprising an effective amount of a compound according to claim 8 together with a pharmaceutically acceptable carrier or diluent.

12. The pharmaceutical composition according to claim 9, 10 or 11 in the form of an oral dosage unit.

13. The pharmaceutical composition according to claim 12, wherein said dosage unit comprises from about 1 to about 100 mg of the compound.

14. The pharmaceutical composition according to claim 9, 10 or 11 in the form of a parenteral dosage unit.

15. The pharmaceutical composition according to claim 14, wherein said dosage unit comprises from about 1 to about 100 mg of the compound.

* * * * *